US008628979B2

(12) United States Patent
Kas

(10) Patent No.: US 8,628,979 B2
(45) Date of Patent: Jan. 14, 2014

(54) MCAM AS A BIOMARKER FOR FLUID HOMEOSTASIS

(75) Inventor: Koen Kas, Schilde (BE)

(73) Assignee: Pronota N.V., Zwijnaarde (BE)

( * ) Notice: Subject to any disclaimer, the term of this patent is extended or adjusted under 35 U.S.C. 154(b) by 0 days.

(21) Appl. No.: 13/502,876

(22) PCT Filed: Oct. 21, 2010

(86) PCT No.: PCT/EP2010/065852
§ 371 (c)(1),
(2), (4) Date: Apr. 19, 2012

(87) PCT Pub. No.: WO2011/048173
PCT Pub. Date: Apr. 28, 2011

(65) Prior Publication Data
US 2012/0237962 A1  Sep. 20, 2012

Related U.S. Application Data

(60) Provisional application No. 61/253,658, filed on Oct. 21, 2009, provisional application No. 61/254,537, filed on Oct. 23, 2009, provisional application No. 61/314,789, filed on Mar. 17, 2010.

(30) Foreign Application Priority Data

Oct. 21, 2009  (EP) .................................... 09173601
Mar. 17, 2010  (EP) .................................... 10156705

(51) Int. Cl.
G01N 33/74    (2006.01)
G01N 33/48    (2006.01)

(52) U.S. Cl.
USPC ....................................................... 436/501

(58) Field of Classification Search
None
See application file for complete search history.

(56) References Cited

U.S. PATENT DOCUMENTS 6,812,339 B1   11/2004  Venter et al.
2007/0264239 A1  11/2007  Huard et al.

FOREIGN PATENT DOCUMENTS

| WO | WO 2004/084921 | | 10/2004 |
|----|----------------|---|---------|
| WO | WO 2006/020936 | | 2/2006 |
| WO | WO 2006/091776 | | 8/2006 |
| WO | WO 2008/131039 | | 10/2008 |
| WO | WO 2010/086405 | * | 8/2010 |
| WO | WO2010/086405 | * | 8/2010 |

OTHER PUBLICATIONS

Larson et al., (2008; Nature Clinical Practice Oncology, vol. 6, No. 2 pp. 105-117).*
Furstenberger et al., (British Journal of Cancer 2005;93,793-798).*
Miller et al., Bailliere's Clinical Endocrinology and Metabolism, pp. 378-379.*
Miller et al., Bailliere's Clinical Endocrinology and Metabolism, 1997; vol. 11 No. 2 pp. 378-379.*
Bardin et al., (Thromb Haemost. Nov. 2003;90(5):915-20).*
Chong et al., (Eur J Heart Fail. Mar. 2006;8(2):167-72. Epub Sep. 26, 2005).*
Bardin et al., (FEBS Letters 1998; vol. 421 pp. 12-14).*
Nesto et al., (Circulation,2003;108:2941-2948).*
Clerico, et al. "Comparison of the Diagnostic Accuracy of Brain Natriuretic Peptide (BNP) and the N-Terminal Part of the Propeptide of BNP Immunoassays in Chronic and Acute Heart Failure: A Systematic Review," Clinical Chemistry, vol. 53, No. 5, pp. 813-822, 2007.
Chan, et al. "Critical Roles of CD146 in Zebrafish Vascular Development," Developmental Dynamics, vol. 232, No. 1, pp. 232-244, Feb. 23, 2006.
International Search Report issued Feb. 10, 2011 to priority international application No. PCT/EP2010/065852.

* cited by examiner

Primary Examiner — Jacob Cheu
Assistant Examiner — Carmencita M Belei
(74) Attorney, Agent, or Firm — Knobbe, Martens, Olson & Bear LLP

(57) ABSTRACT

The application discloses MCAM as a new biomarker for fluid homeostatic imbalance; methods for predicting, diagnosing, prognosticating and/or monitoring fluid homeostatic imbalance based on measuring said biomarker; and kits and devices for measuring said biomarker and/or performing said methods.

13 Claims, 5 Drawing Sheets

FIG 1

MCAM, from NP_006491 mglprlvcafllaacccccprvagvPGEAEQPAPELVEVEVGSTALLKCGLSQSQGNLSHV
DWFSVHKEKRTLIFRVRQGQGQSEPGEYEQRLSLQDRGATLALTQVTPQDERIFLCQGKR
PRSQEYRIQLRVYKAPEEPNIQVNPLGIPVNSKEPEEVATCVGRNGYPIPQVIWYKNGRP
LKEEKNRVHIQSSQTVESSGLYTLQSILKAQLVKEDKDAQFYCELNYRLPSGNHMKESRE
VTVPVFYPTEKVWLEVEPVGMLKEGDRVEIRCLADGNPPPHFSISKQNPSTREAEEETTN
DNGVLVLEPARKEHSGRYECQGLDLDTMISLLSEPQELLVNYVSDVRVSPAAPERQEGSS
LTLTCEAESSQDLEFQWLREETGQVLERGPVLQLHDLKREAGGGYRCVASVPSIPGLNRT
QLVNVAIFGPPWMAFKERKVWVKENMVLNLSCEASGHPRPTISWNVNGTASEQDQDPQRV
LSTLNVLVTPELLETGVECTASNDLGKNTSILFLELVNLTTLTPDSNTTTGLSTSTASPH
TRANSTSTERKLPEPESRGvvivavivcilvlavlgavlyflykkgklpcrrsgkqeitl
Ppsrkselvvevksdklpeemgllqgssgdkrapgdqgekyidlrh (SEQ ID NO: 1)

FIG 3
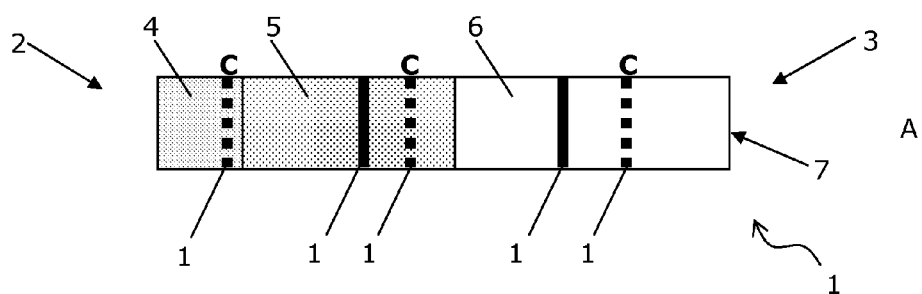
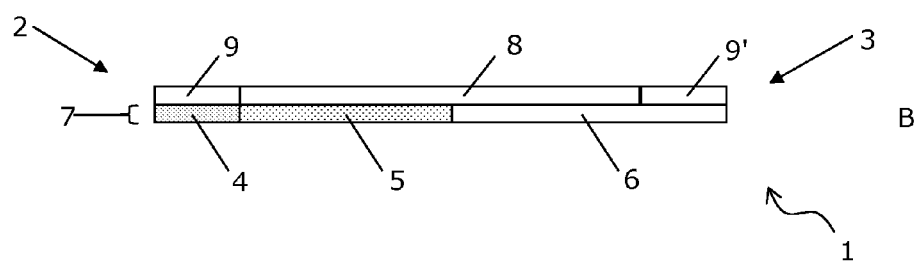
FIG 4
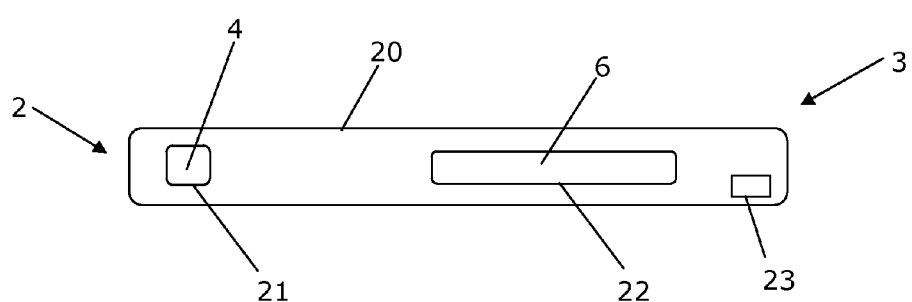

```
                        SEQUENCE LISTING

<160> NUMBER OF SEQ ID NOS: 2

<210> SEQ ID NO 1
<211> LENGTH: 646
<212> TYPE: PRT
<213> ORGANISM: Homo sapiens

<400> SEQUENCE: 1

Met Gly Leu Pro Arg Leu Val Cys Ala Phe Leu Leu Ala Ala Cys Cys
1               5                   10                  15

Cys Cys Pro Arg Val Ala Gly Val Pro Gly Glu Ala Glu Gln Pro Ala
                20                  25                  30

Pro Glu Leu Val Glu Val Glu Val Gly Ser Thr Ala Leu Leu Lys Cys
            35                  40                  45

Gly Leu Ser Gln Ser Gln Gly Asn Leu Ser His Val Asp Trp Phe Ser
        50                  55                  60

Val His Lys Glu Lys Arg Thr Leu Ile Phe Arg Val Arg Gln Gly Gln
    65                  70                  75                  80

Gly Gln Ser Glu Pro Gly Glu Tyr Glu Gln Arg Leu Ser Leu Gln Asp
                85                  90                  95

Arg Gly Ala Thr Leu Ala Leu Thr Gln Val Thr Pro Gln Asp Glu Arg
            100                 105                 110

Ile Phe Leu Cys Gln Gly Lys Arg Pro Arg Ser Gln Glu Tyr Arg Ile
        115                 120                 125

Gln Leu Arg Val Tyr Lys Ala Pro Glu Glu Pro Asn Ile Gln Val Asn
    130                 135                 140

Pro Leu Gly Ile Pro Val Asn Ser Lys Glu Pro Glu Glu Val Ala Thr
145                 150                 155                 160

Cys Val Gly Arg Asn Gly Tyr Pro Ile Pro Gln Val Ile Trp Tyr Lys
                165                 170                 175

Asn Gly Arg Pro Leu Lys Glu Glu Lys Asn Arg Val His Ile Gln Ser
            180                 185                 190

Ser Gln Thr Val Glu Ser Ser Gly Leu Tyr Thr Leu Gln Ser Ile Leu
        195                 200                 205

Lys Ala Gln Leu Val Lys Glu Asp Lys Asp Ala Gln Phe Tyr Cys Glu
    210                 215                 220

Leu Asn Tyr Arg Leu Pro Ser Gly Asn His Met Lys Glu Ser Arg Glu
225                 230                 235                 240

Val Thr Val Pro Val Phe Tyr Pro Thr Glu Lys Val Trp Leu Glu Val
                245                 250                 255

Glu Pro Val Gly Met Leu Lys Glu Gly Asp Arg Val Glu Ile Arg Cys
            260                 265                 270
```

-continued

Leu Ala Asp Gly Asn Pro Pro His Phe Ser Ile Ser Lys Gln Asn
    275                 280                 285

Pro Ser Thr Arg Glu Ala Glu Glu Thr Thr Asn Asp Asn Gly Val
290                 295                 300

Leu Val Leu Glu Pro Ala Arg Lys Glu His Ser Gly Arg Tyr Glu Cys
305                 310                 315                 320

Gln Gly Leu Asp Leu Asp Thr Met Ile Ser Leu Ser Glu Pro Gln
                325                 330                 335

Glu Leu Leu Val Asn Tyr Val Ser Asp Val Arg Val Ser Pro Ala Ala
                340                 345                 350

Pro Glu Arg Gln Glu Gly Ser Ser Leu Thr Leu Thr Cys Glu Ala Glu
            355                 360                 365

Ser Ser Gln Asp Leu Glu Phe Gln Trp Leu Arg Glu Glu Thr Gly Gln
    370                 375                 380

Val Leu Glu Arg Gly Pro Val Leu Gln Leu His Asp Leu Lys Arg Glu
385                 390                 395                 400

Ala Gly Gly Gly Tyr Arg Cys Val Ala Ser Val Pro Ser Ile Pro Gly
                405                 410                 415

Leu Asn Arg Thr Gln Leu Val Asn Val Ala Ile Phe Gly Pro Pro Trp
            420                 425                 430

Met Ala Phe Lys Glu Arg Lys Val Trp Val Lys Glu Asn Met Val Leu
    435                 440                 445

Asn Leu Ser Cys Glu Ala Ser Gly His Pro Arg Pro Thr Ile Ser Trp
450                 455                 460

Asn Val Asn Gly Thr Ala Ser Glu Gln Asp Gln Asp Pro Gln Arg Val
465                 470                 475                 480

Leu Ser Thr Leu Asn Val Leu Val Thr Pro Glu Leu Leu Glu Thr Gly
                485                 490                 495

Val Glu Cys Thr Ala Ser Asn Asp Leu Gly Lys Asn Thr Ser Ile Leu
            500                 505                 510

Phe Leu Glu Leu Val Asn Leu Thr Thr Leu Thr Pro Asp Ser Asn Thr
    515                 520                 525

Thr Thr Gly Leu Ser Thr Ser Thr Ala Ser Pro His Thr Arg Ala Asn
530                 535                 540

Ser Thr Ser Thr Glu Arg Lys Leu Pro Glu Pro Glu Ser Arg Gly Val
545                 550                 555                 560

Val Ile Val Ala Val Ile Val Cys Ile Leu Val Leu Ala Val Leu Gly
                565                 570                 575

Ala Val Leu Tyr Phe Leu Tyr Lys Lys Gly Lys Leu Pro Cys Arg Arg
            580                 585                 590

Ser Gly Lys Gln Glu Ile Thr Leu Pro Pro Ser Arg Lys Ser Glu Leu
    595                 600                 605

Val Val Glu Val Lys Ser Asp Lys Leu Pro Glu Glu Met Gly Leu Leu
610                 615                 620

Gln Gly Ser Ser Gly Asp Lys Arg Ala Pro Gly Asp Gln Gly Glu Lys
625                 630                 635                 640

Tyr Ile Asp Leu Arg His
                645

<210> SEQ ID NO 2
<211> LENGTH: 15
<212> TYPE: PRT
<213> ORGANISM: Homo sapiens

```
<400> SEQUENCE: 2

Gly Ala Thr Leu Ala Leu Thr Gln Val Thr Pro Gln Asp Glu Arg
1               5                   10                  15
```

MCAM AS A BIOMARKER FOR FLUID HOMEOSTASIS

CROSS-REFERENCE TO RELATED APPLICATIONS

This application is the U.S. National Phase under 35 U.S.C. §371 of International Application PCT/EP2010/065852, filed Oct. 21, 2010, which claims priority to EP 09173601.7, filed Oct. 21, 2009, U.S. 61/253,658, filed Oct. 21, 2009, U.S. 61/254,537, filed Oct. 23, 2009, EP 10156705.5, filed Mar. 17, 2010, and U.S. 61/314,789, filed Mar. 17, 2010.

INCORPORATION BY REFERENCE OF SEQUENCE LISTING

The material in the ASCII text filed submitted on Apr. 19, 2012, is incorporated herein by reference. The ACSII text file is named "seq 1st US", created Apr. 9, 2012 and is 71 bytes in size.

FIELD OF THE INVENTION

The invention relates to protein- and/or peptide-based biomarkers and to agents specifically binding thereto, for use in predicting, diagnosing, prognosticating and/or monitoring diseases or conditions in subjects, in particular impaired fluid homeostasis and systolic dysfunction; and to related methods, kits and devices.

BACKGROUND OF THE INVENTION

Maintenance of homeostasis is of crucial importance to the survival of all living organisms. Any organism maintains its structure and functions by means of a multiplicity of dynamic equilibriums rigorously controlled by interdependent regulation mechanisms, in particular positive and negative feedback loops. Such mechanisms are set to react to every change in the environment, or to every random disturbance, through a series of modifications of equal size and opposite direction to those that created the disturbance. The goal of these modifications is to maintain the internal balances. Virtually all physiological processes or systems in mammals, such as humans, are subject to homeostatic monitoring and control. Examples include for instance temperature homeostasis, circadian homeostasis, metabolic homeostasis, endocrine homeostasis, neural homeostasis, respiratory homeostasis, and fluid homeostasis.

On the one hand, many diseases result from disturbance of homeostasis, a condition known as homeostatic imbalance. On the other hand, many diseases in fact cause homeostatic imbalance. Upon aging, every organism will eventually lose efficiency in one or more of its control systems. The inefficiencies gradually result in an unstable internal environment that increases the risk for illness. In addition, homeostatic imbalance is also responsible for the physical changes associated with aging. Even more serious than illness and other characteristics of aging is death. Diseases that result from a homeostatic imbalance, where nominal negative feedback mechanisms become overwhelmed and destructive positive feedback mechanisms then take over, include for example heart failure, diabetes, dehydration, hypoglycemia, hyperglycemia, gout, and any disease caused by a toxin present in the bloodstream. Diseases or disorders which can cause homeostatic imbalance, in particular imbalanced fluid or water homeostasis, include for example hyponatremia, hypernatremia, glucocorticoid deficiency, hypothyroidism, cirrhosis, congestive heart failure and advanced renal failure.

In many diseases and conditions, a favourable outcome of prophylactic and/or therapeutic treatments is strongly correlated with early and/or accurate prediction, diagnosis and/or prognosis and careful monitoring of the disease or condition. Therefore, there exists a continuous need for additional and preferably improved manners for early and/or accurate prediction, diagnosis and/or prognosis and monitoring of diseases and conditions to guide the treatment choices.

It may be clear that accurate and reliable diagnosis, prediction, prognosis and/or monitoring of homeostatic imbalance, and in particular imbalance of fluid or water homeostasis, as well as adequate differentiation between over-filled and under-filled conditions is needed for effective treatment. The present invention addresses the above needs in the art by identifying biomarkers for impaired fluid homeostasis and parameters associated therewith, and providing uses therefore.

Heart failure is a major public health issue in developed countries and is the cause of considerable morbidity and mortality among older adults. Overall, the changes in cardiac function associated with heart failure result in a decrease in cardiac output. It is usually a chronic disease characterised by frequent recurrent decompensation leading to worsening breathing problems. Moreover, 5 years after diagnosis 50% of heart failure patients will have died from the disease.

Several causes underlie heart failure. Specifically systolic dysfunction and diastolic dysfunction lead to cardiac remodelling and altered cardiac function, resulting in a decreased cardiac output. Both dysfunctions are characterized by defects in the pumping function of the heart. Systolic dysfunction results from a loss of intrinsic inotropy (contractility), most likely due to alterations in signal transduction mechanisms responsible for regulating inotropy, and is characterized by defects in emptying the heart, in particular the ventricle, of blood during contraction (i.e. the systole). Diastolic dysfunction occurs when the ventricle becomes less compliant (i.e., "stiffer"), which impairs ventricular filling and as such is characterized by defects in filling the heart, in particular the ventricle, with blood during relaxation (i.e. the diastole).

As such, the pathophysiology of systolic and diastolic dysfunction differs, as intrinsic compensatory mechanisms to cope with both dysfunctions differ. Although systolic and diastolic dysfunction share some common symptoms, the nature of treatment at least partially differs. Whereas both beta blockers and ACE inhibitors are indicated for the treatment of both systolic and diastolic dysfunction, possibly in combination with diuretics, inotropic drugs for instance, such as digoxin, are specifically indicated for the treatment of systolic dysfunction (and contra-indicated for the treatment of diastolic dysfunction) and for instance calcium channel blockers are specifically indicated for the treatment of diastolic dysfunction (and contra-indicated for the treatment of systolic dysfunction).

It may be clear that accurate and reliable diagnosis, prediction, prognosis and/or monitoring of systolic and/or diastolic dysfunction as well as the differentiation between both dysfunctions, is needed for adequate treatment. The present invention addresses the above needs in the art by identifying biomarkers for systolic dysfunction and parameters associated therewith, and providing uses therefore.

SUMMARY OF THE INVENTION

Having conducted extensive experiments and tests, the inventors have revealed that melanoma cell adhesion molecule (MCAM, also known as CD146 or MUC18) represents a new biomarker advantageous for evaluating fluid homeostasis, specifically for predicting, diagnosing, prognosticating and/or monitoring homeostatic imbalance, in particular impaired body fluid homeostasis and associated parameters.

The inventors have found that MCAM levels correlate with the fluid filling status of a subject. MCAM levels were found to be elevated in subjects with high fluid content or fluid retention i.e. impaired body fluid/water homeostasis, compared to subjects with comparably lower fluid content, i.e. normal body fluid/water homeostasis.

Hence, provided is a method for determining fluid homeostasis in a subject comprising measuring the quantity of MCAM in a sample from said subject; particularly provided is a method for predicting, diagnosing, prognosticating and/or monitoring impaired fluid or water homeostasis in a subject, comprising measuring MCAM levels in a sample from said subject.

As used throughout this specification, measuring the levels of MCAM and/or other biomarker(s) in a sample from a subject may particularly denote that the examination phase of a method comprises measuring the quantity of MCAM and/or said other biomarker(s) in the sample from the subject. One understands that methods of prediction, diagnosis, prognosis and/or monitoring of diseases, conditions, symptoms or parameter values generally comprise an examination phase in which data is collected from and/or about the subject.

In an embodiment, said method for predicting, diagnosing and/or prognosticating impaired fluid homeostasis comprises the steps of:
(i) measuring the quantity of MCAM in a sample from the subject;
(ii) comparing the quantity of MCAM measured in (i) with a reference value of the quantity of MCAM, said reference value representing a known prediction, diagnosis and/or prognosis of impaired or normal fluid homeostasis;
(iii) finding a deviation or no deviation of the quantity of MCAM measured in (i) from the reference value;
(iv) attributing said finding of deviation or no deviation to a particular prediction, diagnosis and/or prognosis of impaired fluid homeostasis in the subject.

In an embodiment, said method for monitoring (impaired) fluid homeostasis comprises the steps of:
(i) measuring the quantity of MCAM in samples from the subject from two or more successive time points;
(ii) comparing the quantity of MCAM between the samples as measured in (i);
(iii) finding a deviation or no deviation of the quantity of MCAM between the samples as compared in (ii);
(iv) attributing said finding of deviation or no deviation to a change in (impaired) fluid homeostasis in the subject between the two or more successive time points.

The monitoring may be applied in the course of a medical treatment of the subject.

The present methods measuring MCAM as a biomarker can therefore determine whether a subject is over-filled or hypervolemic (i.e., has increased vascular filling volume or pressure or is subject to fluid build-up or volume overload); or whether a subject is under-filled or hypovolemic (i.e., has decreased vascular filling volume or pressure or is subject to fluid drainage or volume contraction); or whether a subject has normal filling volume or pressure (euvolemic).

In an embodiment, an increased or decreased quantity (i.e., a deviation) of MCAM in the sample from the subject compared to a reference value representing the diagnosis or prediction of not impaired (i.e., normal, euvolemic) fluid homeostasis or representing a good prognosis for impaired fluid homeostasis indicates that the subject has or is at risk of having impaired fluid homeostasis or indicates a poor prognosis for impaired fluid homeostasis in the subject. In an embodiment an increased quantity of MCAM in the sample from the subject compared to said euvolemic reference value indicates that the subject is over-filled or is at risk of becoming over-filled or indicates a poor prognosis for said over-filling in the subject. In another embodiment a decreased quantity of MCAM in the sample from the subject compared to said euvolemic reference value indicates that the subject is under-filled or is at risk of becoming under-filled or indicates a poor prognosis for said under-filling in the subject.

Alternatively, a comparable quantity (i.e., no deviation) of MCAM in the sample from the subject compared to a reference value representing the diagnosis or prediction of not impaired (i.e., normal, euvolemic) fluid homeostasis or representing a good prognosis for impaired fluid homeostasis indicates that the subject does not have or is not at risk of having impaired fluid homeostasis or indicates a good prognosis for impaired fluid homeostasis in the subject. Alternatively, a comparable (i.e., no deviation) quantity of MCAM in the sample from the subject compared to a reference value representing the diagnosis or prediction of impaired fluid homeostasis or representing a poor prognosis for impaired fluid homeostasis indicates that the subject has or is at risk of having impaired fluid homeostasis or indicates a poor prognosis for impaired fluid homeostasis in the subject.

In an embodiment of the fluid homeostasis monitoring method as taught herein, an increase or decrease in the quantity of MCAM in a sample from a later one of the successive time points relative to a sample from an earlier one of the successive time points is indicative of respectively an increase or decrease in vascular filling volume or pressure in the subject between said later vs. earlier time points. Without limitation, an increase in vascular filling volume or pressure may be detrimental (e.g., in a patient suffering from over-filling) or beneficial (e.g., in a patient suffering from under-filling). A decrease in vascular filling volume or pressure may be detrimental (e.g., in a patient suffering from under-filling) or beneficial (e.g., in a patient suffering from over-filling).

In an embodiment, said filling status or fluid homeostasis is represented by vascular filling volume or vascular filling pressure (used interchangeably throughout the specification) of the subject. In a further embodiment, said filling status or fluid homeostasis is represented by the weight of the subject Hence, in an embodiment, weight gain represent edema, such as pulmonary edema, or edema of the lower extremities, and weight loss represent dehydration. Edema or dehydration may be connected to weight gain or weight loss, respectively, particularly in an over-filling situation.

Hence, in an aspect, the invention relates to a method to determine whether a subject is or is not (such as, for example, still is, or is no longer) in need of a therapy to treat impaired fluid homeostasis, comprising:
(i) measuring the quantity of MCAM in the sample from the subject;
(ii) comparing the quantity of MCAM measured in (i) with a reference value of the quantity of MCAM, said reference value representing a known diagnosis, prediction and/or prognosis of impaired or normal fluid homeostasis;
(iii) finding a deviation or no deviation of the quantity of MCAM measured in (i) from said reference value;
(iv) inferring from said finding the presence or absence of a need for a therapy to treat impaired fluid homeostasis.µ

By means of an example and not limitation, a patient having impaired fluid homeostasis upon admission to or during stay in a medical care centre may be tested as taught herein for the necessity of continuing a treatment of said impaired fluid homeostasis, and may be discharged when such treatment is no longer needed or is needed only to a given limited extent.

In an embodiment, said therapy is:

(i) a therapy to restore fluid homeostasis by decreasing the vascular filling volume or pressure or reversing weight gain due to fluid build-up, if the quantity of MCAM in said sample is higher than said reference value, wherein said reference value represents normal (euvolemic) fluid homeostasis and/or the reference value represents a threshold value above which value is indicative of the need for a therapy to decrease the vascular filling volume or to reverse weight gain due to fluid build-up; or (ii) a therapy to restore fluid homeostasis by increasing the vascular filling volume or pressure or reversing weight loss due to fluid drainage, if the quantity of MCAM in said sample is lower than said reference value, wherein said reference value represents normal (euvolemic) fluid homeostasis and/or the reference value represents a threshold value below which value is indicative of the need for a therapy to increase the vascular filling volume or to reverse weight loss due to fluid drainage.

In a further aspect, the present invention also relates to a method to determine whether a subject is or is not in need of a therapy to adjust the filling status or the vascular filling volume or pressure comprising:

(i) measuring the quantity of MCAM in the sample from the subject;

(ii a) comparing the quantity of MCAM measured in (i) with a reference value of the quantity of MCAM, said reference value representing a threshold value above which value is indicative of the need for a therapy to decrease the fluid content (decrease the vascular filling volume or pressure); and/or (ii b) comparing the quantity of MCAM measured in (i) with a reference value of the quantity of MCAM, said reference value representing a threshold value below which value is indicative of the need for a therapy to increase the fluid content (increase the vascular filling volume or pressure); and (iii a) inferring from a higher MCAM value in said sample compared to said reference value in (ii a) the need for a therapy to decrease the fluid content in said subject or the need to stop a therapy to increase the fluid content; and/or (iii b) inferring from a lower MCAM value in said sample compared to said reference value in (ii b) the need for a therapy to increase the fluid content in said subject or the need to stop a therapy to decrease the fluid content.

In an embodiment, said therapy to the restore fluid homeostasis by decreasing the fluid content, the vascular filling volume or pressure and/or reversing weight gain due to fluid build-up comprises administrating exogenous and/or endogenous diuretic agents and/or ultrafiltration to remove salts and the corresponding fluid from the circulation. Examples of diuretics which can be used according to the invention include but are not limited to are acidifying salts such as $CaCl_2$ and $NH_4Cl$; arginine vasopressin receptor 2 antagonists such as amphotericin B and lithium citrate inhibit vasopressin's action; aquaretics such as Goldenrod and Juniper; Na—H exchanger antagonists such as dopamine; carbonic anhydrase inhibitors such as acetazolamide and dorzolamide; loop diuretics such as bumetanide[, ethacrynic acid, furosemide and torsemide; osmotic diuretics such as glucose (especially in uncontrolled diabetes) and mannitol; potassium-sparing diuretics such as amiloride, spironolactone, triamterene and potassium canrenoate; thiazides such as bendroflumethiazide and hydrochlorothiazide; xanthines such as caffeine, theophylline and theobromine.

In another embodiment, said therapy to restore fluid homeostasis by increasing the fluid content, the vascular filling volume or pressure and/or reversing weight loss due to fluid drainage comprises administrating exogeneous and/or endogenous antidiuretic or vassopressive agents. Examples of antidiuretics which can be used according to the invention include but are not limited to antidiuretic hormones such as ADH/vasopressin, desmopressin, lypressin and terlipressin; non-hormone diuretics such as chlorpropamide and carbamazepine.

The present methods may inter alia allow to identify patients having dyspnea due to volume overload, and may preferably discriminate such patients from dyspnea due to other causes (such as, e.g., COPD or pneumonia). Over-filled patients may be indicative of heart failure (HF) and at risk of decompensation into acute heart failure (AHF).

Further, the study by Komajda et al. 2010 (Eur Heart J, doi: 10.1093/eurheartj/ehp604) reports that treatment with the thiazolidinedione rosiglitazone is associated with fluid retention and increased risk of HF in people with type 2 diabetes in the RECORD trial population, and supports the recommendation that this agent should not continue to be used in people developing symptomatic HF while using the medication.

Also contemplated are thus methods for predicting, diagnosing, prognosticating and/or monitoring impaired fluid homeostasis (preferably volume overload) comprising measuring the quantity of MCAM in a subject as taught herein, wherein the subject is receiving or has received an anti-diabetes treatment, more particularly one or more insulin sensitizers, preferably one or more agonists of peroxisome proliferator-activated receptor gamma (PPAR-gamma) (e.g., PPAR-gamma 1, 2 and/or 3), more preferably one or more thiazolidinediones (glitazones) such as preferably but without limitation rosiglitazone and/or pioglitazone.

Hence, the invention contemplates MCAM, more particularly the quantity of MCAM, as a companion diagnostic marker for impaired fluid homeostasis (preferably volume overload) in subjects receiving or having received such antidiabetes treatment. The anti-diabetes treatment may be known or suspected of association with fluid retention (volume overload), HF or AHF, i.e., causing such condition(s) as potential side effects.

The herein disclosed methods for predicting, diagnosing, prognosticating and/or monitoring impaired fluid homeostasis comprising measuring the quantity of MCAM in a subject, may also be employed to stratify or categorise patients receiving or having received an anti-diabetes treatment as taught herein to identify those patients having or being at risk of having impaired fluid homeostasis or having a poor prognosis for impaired fluid homeostasis, and therefore likely to respond to (i.e., benefit from) a therapy to restore fluid homeostasis. In particular, the impairment of fluid homeostasis may be volume overload, and the stratification can identify responders to volume-reducing therapies.

The inventors have further found that MCAM levels correlate with left ventricular ejection fraction (LVEF). Subjects with a reduced LVEF have been shown to have altered (esp. increased) MCAM levels, compared to subjects with normal LVEF. As reduced LVEF is a hallmark for systolic dysfunction, MCAM levels can be used to predict, diagnose, prognosticate and/or monitor systolic dysfunction.

In particular, in a 3-centre study involving prospective collection of samples from subjects presenting with dyspnea upon emergency admission, MCAM was significantly increased in dyspneic patients (esp. AHF patients) showing reduced LVEF indicative of systolic dysfunction, compared to dyspneic patients with preserved LVEF and systolic function. Systolic dysfunction may preferably denote systolic dysfunction of the left ventricle.

In another aspect, the invention hence relates to a method for predicting, diagnosing, prognosticating and/or monitoring systolic dysfunction in a subject, comprising measuring MCAM levels in a sample from said subject.

Furthermore, in the above population of AHF patients with a predominance of heart failure patients with systolic dysfunction, the AUC value (area under the ROC curve; "ROC" stands for receiver operating characteristic) for discriminating between the dyspneic patients with and without AHF, is slightly higher for MCAM (0.91) than for each one of BNP (0.88) and NT-proBNP (0.85). The AUC value is a combined measure of sensitivity and specificity and a higher AUC value (i.e., approaching 1) in general indicates an improved performance of the test.

The inventors have further found that MCAM levels correlate with cardiac filling status. In particular, the inventors have found that MCAM levels are higher in subjects with an increased cardiac filling pressure, compared to subjects with normal cardiac filling pressure.

Both systolic and diastolic dysfunction can cause fluid build-up in a subject. Subjects with a systolic dysfunction however, are more resistant to fluid build-up and hence will accumulate more volume compared to patients with diastolic dysfunction before symptoms such as dyspnea occur. The inventors have found that MCAM levels correlate with fluid build-up, and in particular the vascular filling status or vascular filling volume or pressure as a measurement of fluid homeostasis. In particular, the inventors found that MCAM levels are higher in subjects with an increased vascular filling volume or pressure and hence MCAM is a marker for fluid build-up in a subject. As a corollary, MCAM levels are associated to weight gain due to over-filling or weight loss due to under-filling or volume contraction of a subject. As such, the inventors have found that MCAM is a marker for determining oedema, changes in volume status or dehydration in a subject. In particular, MCAM levels are correlated with the filling status of a subject with defects in blood circulation, such as caused by heart failure, and defects in secretion, such as caused by kidney dysfunction or kidney failure. Accordingly, in an embodiment, the invention relates to a method as described herein for diagnosing, predicting, prognosticating and/or monitoring an impaired fluid homeostasis in a subject, wherein the subject presents itself with, is diagnosed with or has a medical history of heart failure, in particular systolic dysfunction.

Provided is thus a method for predicting, diagnosing, prognosticating and/or monitoring dyspnea associated with or caused by volume overload comprising measuring MCAM levels in a sample from said subject. Volume overload may be indicative of HF, preferably HF due to systolic dysfunction, and may be at risk of decompensation or having decompensated into AHF. The method can discriminate dyspnea caused by volume overload such as HF or AHF from other causes of dyspnea (e.g., COPD, pneumonia).

Disclosed is also a method for predicting, diagnosing, prognosticating and/or monitoring HF, preferably AHF, associated with or caused by volume overload in a subject, comprising measuring MCAM levels in a sample from said subject. The volume overload may be due to systolic dysfunction.

Hence, disclosed is also a method for predicting, diagnosing, prognosticating and/or monitoring HF, preferably AHF, associated with or caused by systolic dysfunction in a subject, comprising measuring MCAM levels in a sample from said subject.

Systolic dysfunction is characterized by a decreased ejection fraction of the left and/or right ventricle, more particularly decreased LVEF. The inventors have found that MCAM levels are correlated with the ventricular ejection fraction. Disclosed is thus also a method for predicting, diagnosing, prognosticating and/or monitoring the ventricular ejection fraction in a subject, comprising measuring MCAM levels in a sample from said subject.

A ventricular ejection fraction (e.g., LVEF) in a subject may be said to be reduced compared to normal, if said ejection fraction is below normal by any extent, e.g., a reduced ventricular ejection fraction may mean less than about 45% or less than about 50% or less than about 55%; for example a reduced ventricular ejection fraction may denote between about 40% and about 70%, preferably between about 45% and about 65%, or between about 50% and about 60%, e.g., less than about 55%. In an exemplary but non-limiting experiment MCAM levels provided particularly satisfactory discrimination between normal and reduced LVEF when the threshold between said normal and reduced LVEF was set at 55%. Hence, in embodiments a threshold for normal vs. reduced ventricular ejection fraction, in particular LVEF, may be set at a value between about 50% and about 60%, e.g., at 50%, 51%, 52%, 53%, 54%, 55%, 56%, 57%, 58%, 59% or 60%, and preferably at 55%, wherein a value above said threshold reflects normal ejection fraction and a value below said threshold denotes reduced ejection fraction. This reduced LVEF may also be reflected in an increased LVEDP (left ventricular end-diastolic pressure), the preload pressure in the left ventricle, prior to contraction of the ventricle.

The drop or decrease in cardiac output due to a decreased ventricular ejection fraction promotes renal salt and water retention. This appropriate adaptation expands the blood volume, thereby raising end-diastolic pressure (e.g. LVEDP) and volume. Thus, systolic dysfunction is also characterized by an increased cardiac filling pressure. Hence, provided is also a method for predicting, diagnosing, prognosticating and/or monitoring the cardiac filling status in a subject comprising measuring MCAM levels in a sample from said subject. Cardiac filling status may be represented by the cardiac filling pressure.

Hence, provided is a method for predicting, diagnosing and/or prognosticating systolic dysfunction in a subject that may comprise the steps:
(i) measuring the quantity of MCAM in a sample from the subject;
(ii) comparing the quantity of MCAM measured in (i) with a reference value of the quantity of MCAM, said reference value representing a known prediction, diagnosis and/or prognosis of systolic dysfunction;
(iii) finding a deviation or no deviation of the quantity of MCAM measured in (i) from the reference value;
(iv) attributing said finding of deviation or no deviation to a particular prediction, diagnosis and/or prognosis of systolic dysfunction in the subject.

The above steps can be applied mutatis mutandis to dyspnea associated with or caused by volume overload; to HF or AHF associated with or caused by volume overload; to HF or AHF associated with or caused by systolic dysfunction; to ventricular ejection fraction; or to cardiac filling status.

MCAM provides an improved or even substantially complete discrimination of dyspnea caused by volume overload such as AHF from other causes of dyspnea. Therefore, the inventors contemplate that MCAM can also be beneficial for population screening setups to select subjects having or being at risk of having an acute decompensation. Any one of the herein described methods may be employed for population screening (such as, e.g., screening in a general population or in a population stratified based on one or more criteria, e.g., age, gender, ancestry, occupation, presence or absence of risk factors of AHF, etc.). In any one the above methods of the present invention, the subject may form part of a patient population showing signs of dyspnea.

The inventors have found that MCAM can be used as a specific biomarker for systolic dysfunction. Hence, in an aspect, the invention relates to the use of the methods as described herein for discriminating between systolic and diastolic dysfunction.

In an embodiment, provided is a method for discriminating between systolic dysfunction and diastolic dysfunction in a subject, comprising:
(i) measuring the quantity of MCAM in a sample from said subject;
(ii) comparing the quantity of MCAM measured in (i) with a reference value of the quantity of MCAM, said reference value representing a threshold for the diagnosis of systolic dysfunction;
(iii) attributing the diagnosis of systolic dysfunction in said subject if the quantity of MCAM in said sample of said subject exceeds said threshold.

As demonstrated in the experimental section, the inventors have shown that prediction or diagnosis of systolic dysfunction or a poor prognosis of systolic dysfunction can in particular be associated with an elevated level of MCAM. Hence, in an embodiment of the prediction, diagnosis and/or prognosis methods as taught herein, an elevated quantity of MCAM in the sample from the subject compared to a reference value representing the prediction or diagnosis of no systolic dysfunction or representing a good prognosis for systolic dysfunction respectively indicates that the subject has or is at risk of having systolic dysfunction or indicates a poor prognosis for systolic dysfunction in the subject. Elevated MCAM levels may also be indicative of prediction or diagnosis or poor prognosis of dyspnea associated with or caused by volume overload; or of HF or AHF associated with or caused by volume overload; or of HF or AHF associated with or caused by systolic dysfunction; or of reduced ventricular ejection fraction; or of increased cardiac filling pressure.

In an embodiment, the method for monitoring systolic dysfunction comprises the steps of:
(i) measuring the quantity of MCAM in samples from the subject from two or more successive time points;
(ii) comparing the quantity of MCAM between the samples as measured in (i);
(iii) finding a deviation or no deviation of the quantity of MCAM between the samples as compared in (ii);
(iv) attributing said finding of deviation or no deviation to a change in systolic dysfunction in the subject between the two or more successive time points.

The above steps can be applied mutatis mutandis to dyspnea associated with or caused by volume overload; to HF or AHF associated with or caused by volume overload; to HF or AHF associated with or caused by systolic dysfunction; to ventricular ejection fraction; or to cardiac filling status.

The monitoring may be applied in the course of a medical treatment of the subject.

In an embodiment of the prediction, diagnosis, prognosis and/or monitoring methods as taught herein, the sensitivity and/or specificity (and preferably, the sensitivity and specificity) of the methods is at least 50%, at least 60%, at least 70% or at least 80%, e.g., ≥81%, ≥82%, ≥83%, ≥84%, ≥85%, ≥86%, or ≥87%, or ≥90% or ≥95% (symbol "≥" is synonymous with expressions "at least" or "equal to or more"), e.g., between 80% and 100%, or between 81% and 95%, or between 83% and 90%, or between 84% and 89%, or between 85% and 88%.

In another embodiment of the prediction, diagnosis, prognosis and/or monitoring methods as taught herein, the subject may present itself with one or more symptoms and/or signs potentially indicative of fluid homeostatic imbalance, acute heart failure, chronic heart failure, systolic dysfunction or kidney dysfunction or failure. For example, in an embodiment the subject may present itself with dyspnea.

In a further embodiment of the prediction, diagnosis, prognosis and/or monitoring methods as taught herein, the subject may display one or more risk factors for the conditions, symptoms and/or parameter values according to the invention, such as, for example, a genetic predisposition or one or more developmental, environmental or behavioural risk factors, such as, e.g., insulin resistance (impaired blood glucose), truncal obesity, high serum low density lipoprotein (LDL) cholesterol levels, low serum high density lipoprotein (HDL) cholesterol levels, high serum triglyceride levels, and high blood pressure (hypertension), prior myocardial infarctus, and/or one or more co-morbidities, such as diabetes, coronary artery disease, asthma, COPD and/or chronic renal disease.

Reference throughout this specification to "conditions, symptoms and/or parameter values" encompasses any such conditions, symptoms and/or parameter values as disclosed herein, such as in particular but without limitation impaired fluid homeostasis and related changes in weight (e.g., edema or dehydration) and in vascular filling volume or pressure (e.g. elevated LVEDP); and further systolic dysfunction; dyspnea associated with or caused by volume overload; HF or AHF associated with or caused by volume overload; HF or AHF associated with or caused by systolic dysfunction; ventricular ejection fraction (e.g., LVEF); and cardiac filling status.

The present methods for predicting, diagnosing, prognosticating and/or monitoring the conditions, symptoms and/or parameter values according to the invention may be used in individuals who have not yet been diagnosed as having such (for example, preventative screening), or who have been diagnosed as having such, or who are suspected of having such (for example, display one or more characteristic symptoms), or who are at risk of developing such (for example, genetic predisposition; presence of one or more developmental, environmental or behavioural risk factors). The methods may also be used to detect various stages of progression or severity of the conditions, symptoms and/or parameter values according to the invention. The methods may also be used to detect response of the conditions, symptoms and/or parameter values according to the invention to prophylactic or therapeutic treatments or other interventions. The methods can furthermore be used to help the medical practitioner in deciding upon worsening, status-quo, partial recovery, or complete recovery of the patient from the conditions, symptoms and/or parameter values according to the invention, resulting in either further treatment or observation or in discharge of the patient from the ED.

The methods of the present invention enable the medical practitioner to monitor the disease progress by measuring the level of MCAM in a sample of the patient.

For example, in patients suffering from over-filling (volume overload), a decrease in MCAM level as compared to a prior MCAM level (e.g. at the time of the admission to the ED) indicates the condition of the subject is improving or has improved, while an increase of the MCAM level as compared to a prior MCAM level (e.g. at the time of the admission to the ED) indicates the condition of the subject has worsened or is worsening. Such worsening could possibly result in the recurrence of the conditions, symptoms and/or parameter values according to the invention, such as in a new acute heart failure event.

In another example, in patients suffering from under-filling (volume contraction), such as for example Intensive Care Unit patients, an increase in MCAM level as compared to a prior MCAM level (e.g. at the time of the admission to the ICU) indicates the condition of the subject is improving or has improved, while a decrease of the MCAM level as compared to a prior MCAM level (e.g. at the time of the admission to the ICU) indicates the condition of the subject has worsened or is worsening.

Accordingly, further provided are a method for monitoring a change in the prediction, diagnosis and/or prognosis of the conditions, symptoms and/or parameter values according to the invention in a subject, comprising:
  (i) applying the prediction, diagnosis and/or prognosis method as taught here above to the subject at two or more successive time points, whereby the prediction, diagnosis and/or prognosis of the conditions, symptoms and/or parameter values according to the invention in the subject is determined at said successive time points;
  (ii) comparing the prediction, diagnosis and/or prognosis of the conditions, symptoms and/or parameter values according to the invention in the subject at said successive time points as determined in (i); and
  (iii) finding the presence or absence of a change between the prediction, diagnosis and/or prognosis of the conditions, symptoms and/or parameter values according to the invention in the subject at said successive time points as determined in (i).

This aspect allows to monitor the subject's condition over time. This can inter alia allow to predict the occurrence the conditions, symptoms and/or parameter values according to the invention, or to monitor in said subject the disease progression, disease aggravation or alleviation, disease recurrence, response to treatment, response to other external or internal factors, conditions, or stressors, etc. Advantageously, the change in the prediction, diagnosis and/or prognosis in the subject may be monitored in the course of a medical treatment of said subject. Such monitoring may be comprised, e.g., in decision making whether a patient may be discharged, needs a change in treatment or needs further hospitalisation.

It shall be appreciated that in the present prediction, diagnosis, prognosis and/or monitoring methods the measurement of MCAM may also be combined with the assessment of one or more further biomarkers or clinical parameters relevant for the conditions, symptoms and/or parameters according to the invention.

Consequently, also disclosed herein are methods, wherein the examination phase of the methods further comprises measuring the presence or absence and/or quantity of one or more such other biomarkers in the sample from the subject. In this respect, any known or yet unknown suitable marker could be used.

A reference throughout this specification to biomarkers "other than MCAM" or "other biomarkers" generally encompasses such other biomarkers which are useful for predicting, diagnosing, prognosticating and/or monitoring the conditions, symptoms and/or parameter values as disclosed herein, and may preferably denote markers selected from the group consisting of: natriuretic peptides such as atrial natriuretic peptide (ANP), pro-ANP, mid-regional portion of pro-ANP (MR-proANP), B-type natriuretic peptide (BNP), pro-B-type natriuretic peptide (proBNP), amino terminal pro-B-type natriuretic peptide (NTproBNP), Cystatin C, neutrophil gelatinase-associated lipocalin (NGAL), Albumin (more particularly U-Albumin), γ-glutamyl transpeptidase (γ-GT), N-Acetyl-beta-(D)-Glucosaminidase (NAG), alpha-1-microglobulin (A1M), beta-2-microglobulin (B2M), urea, creatinine, vasopressin, aldosteron, copeptin, angiotensin, ACE and fragments of any one thereof.

Hence, disclosed is a method for predicting, diagnosing and/or prognosticating the conditions, symptoms and/or parameter values according to the invention in a subject comprising the steps:
  (i) measuring the quantity of MCAM and the presence or absence and/or quantity of said one or more other biomarkers in the sample from the subject;
  (ii) using the measurements of (i) to establish a subject profile of the quantity of MCAM and the presence or absence and/or quantity of said one or more other biomarkers;
  (iii) comparing said subject profile of (ii) to a reference profile of the quantity of MCAM and the presence or absence and/or quantity of said one or more other biomarkers, said reference profile representing a known prediction, diagnosis and/or prognosis of the conditions, symptoms and/or parameter values according to the invention;
  (iv) finding a deviation or no deviation of the subject profile of (ii) from the reference profile;
  (v) attributing said finding of deviation or no deviation to a particular prediction, diagnosis and/or prognosis of the conditions, symptoms and/or parameter values according to the invention in the subject.

Applying said method at two or more successive time points allows for monitoring the desired conditions, symptoms and/or parameter values.

In preferred embodiments of the methods of the present invention, the MCAM protein detection is done in a plasma sample (i.e. a non-blood-cell containing blood sample fraction), implying that the circulating MCAM protein is detected, regardless of whether or not this circulating form corresponds to the MMP-processed soluble form or to a degradation product of the full-length or of said soluble form of MCAM. In a preferred embodiment, the MCAM protein detected is not membrane or cell-bound, but rather is the plasma circulating form of MCAM, regardless of how release of MCAM into plasma or serum is achieved in vivo.

As indicated above, the present methods may employ reference values for the quantity of MCAM, which may be established according to known procedures previously employed for other biomarkers. Such reference values may be established either within (i.e., constituting a step of) or external to (i.e., not constituting a step of) the methods of the present invention as defined herein. Accordingly, any one of the methods taught herein may comprise a step of establishing a reference value for the quantity of MCAM, said reference value representing either (a) a prediction or diagnosis of the absence of the conditions, symptoms and/or parameter values according to the invention or a good prognosis thereof, or (b) a prediction or diagnosis of the conditions, symptoms and/or parameter values according to the invention or a poor prognosis thereof.

A further aspect provides a method for establishing a reference value for the quantity of MCAM, said reference value representing:
  (a) a prediction or diagnosis of the absence of the conditions, symptoms and/or parameter values according to the invention or a good prognosis thereof, or (b) a prediction or diagnosis of the conditions, symptoms and/or parameter values according to the invention or a poor prognosis thereof, comprising:
(i) measuring the quantity of MCAM in:
(i a) one or more samples from one or more subjects not having the conditions, symptoms and/or parameter values according to the invention or not being at risk of having such or having a good prognosis for such, or
(i b) one or more samples from one or more subjects having the conditions, symptoms and/or parameter values according to the invention or being at risk of having such or having a poor prognosis for such, and
(ii) storing the quantity of MCAM
(ii a) as measured in (i a) as the reference value representing the prediction or diagnosis of the absence of the conditions, symptoms and/or parameter values according to the invention or representing the good prognosis therefore, or
(ii b) as measured in (i b) as the reference value representing the prediction or diagnosis of the conditions, symptoms and/or parameter values according to the invention or representing the poor prognosis therefore.

The present methods may otherwise employ reference profiles for the quantity of MCAM and the presence or absence and/or quantity of one or more other biomarkers, which may be established according to known procedures previously employed for other biomarkers. Such reference profiles may be established either within (i.e., constituting a step of) or external to (i.e., not constituting a step of) the present methods. Accordingly, the methods taught herein may comprise a step of establishing a reference profile for the quantity of MCAM and the presence or absence and/or quantity of said one or more other biomarkers, said reference profile representing either (a) a prediction or diagnosis of the absence of the conditions, symptoms and/or parameter values according to the invention or a good prognosis therefore, or (b) a prediction or diagnosis of the conditions, symptoms and/or parameter values according to the invention or a poor prognosis therefore.

A further aspect provides a method for establishing a reference profile for the quantity of MCAM and the presence or absence and/or quantity of one or more other biomarkers useful for predicting, diagnosing, prognosticating and/or monitoring the conditions, symptoms and/or parameter values according to the invention said reference profile representing:
(a) a prediction or diagnosis of the absence of the conditions, symptoms and/or parameter values according to the invention or a good prognosis therefore, or
(b) a prediction or diagnosis of the conditions, symptoms and/or parameter values according to the invention or a poor prognosistherefore, comprising:
(i) measuring the quantity of MCAM and the presence or absence and/or quantity of said one or more other biomarkers in:
(i a) one or more samples from one or more subjects not having the conditions, symptoms and/or parameter values according to the invention or not being at risk of having such or having a good prognosis for such; or
(i b) one or more samples from one or more subjects having the conditions, symptoms and/or parameter values according to the invention or being at risk of having such or having a poor prognosis for such;

(ii)
(ii a) using the measurements of (i a) to create a profile of the quantity of MCAM and the presence or absence and/or quantity of said one or more other
(ii b) using the measurements of (i b) to create a profile of the quantity of MCAM and the presence or absence and/or quantity of said one or more other biomarkers;
(iii)
(iii a) storing the profile of (ii a) as the reference profile representing the prediction or diagnosis of the absence of the conditions, symptoms and/or parameter values according to the invention or representing the good prognosis therefore; or
(iii b) storing the profile of (ii b) as the reference profile representing the prediction or diagnosis of the conditions, symptoms and/or parameter values according to the invention or representing the poor prognosis therefore.

The invention further provides a method for establishing a MCAM base-line or reference value in a subject, comprising:
(i) measuring the quantity of MCAM in the sample from the subject at different time points wherein the subject is not suffering from the conditions, symptoms and/or parameter values according to the invention, and
(ii) calculating the range or mean value of the subject, which is the MCAM base-line or reference value for said subject.

In preferred embodiments of any one of above methods the subject may be human.

In the methods taught herein, the quantity of MCAM and/or the presence or absence and/or quantity of the one or more other biomarkers may be measured by any suitable technique such as may be known in the art.

In an embodiment, the quantity of MCAM and/or the presence or absence and/or quantity of the one or more other biomarkers may be measured using, respectively, a binding agent capable of specifically binding to MCAM and/or to fragments thereof, and a binding agent capable of specifically binding to said one or more other biomarkers. In an embodiment, the binding agent may be an antibody, aptamer, photoaptamer, protein, peptide, peptidomimetic or a small molecule.

In a further embodiment, the quantity of MCAM and/or the presence or absence and/or quantity of the one or more other biomarkers is measured using an immunoassay technology, such as direct ELISA, indirect ELISA, sandwich ELISA, competitive ELISA, multiplex ELISA, radioimmunoassay (RIA) or ELISPOT technologies, or using a mass spectrometry analysis method or using a chromatography method, or using a combination of said methods.

In an embodiment, in the methods as taught herein, the subject has a medical history of the conditions, symptoms and/or parameter values according to the invention. In a further embodiment, the subject has a medical history of acute or chronic heart failure. In yet another embodiment, the subject has a medical history of kidney dysfunction or failure.

Another aspect discloses a kit for predicting, diagnosing, prognosticating and/or monitoring the conditions, symptoms and/or parameter values according to the invention in a subject, the kit comprising (i) means for measuring the quantity of MCAM in a sample from the subject, and optionally and preferably (ii) a reference value of the quantity of MCAM or means for establishing said reference value, wherein said reference value represents a known prediction, diagnosis and/or prognosis of the conditions, symptoms and/or parameter values according to the invention.

The kit thus allows one to: measure the quantity of MCAM in the sample from the subject by means (i); compare the quantity of MCAM measured by means (i) with the reference value of (ii) or established by means (ii); find a deviation or no deviation of the quantity of MCAM measured by means (i) from the reference value of (ii); and consequently attribute said finding of deviation or no deviation to a particular prediction, diagnosis and/or prognosis of the conditions, symptoms and/or parameter values according to the invention in the subject.

A further embodiment provides a kit for predicting, diagnosing, prognosticating and/or monitoring the conditions, symptoms and/or parameter values according to the invention in a subject, the kit comprising (i) means for measuring the quantity of MCAM in a sample from the subject and (ii) means for measuring the presence or absence and/or quantity of one or more other biomarkers in the sample from the subject, and optionally and preferably (iii) means for establishing a subject profile of the quantity of MCAM and the presence or absence and/or quantity of said one or more other biomarkers, and optionally and preferably (iv) a reference profile of the quantity of MCAM and the presence or absence and/or quantity of said one or more other biomarkers, or means for establishing said reference profile, said reference profile representing a known prediction, diagnosis and/or prognosis of the conditions, symptoms and/or parameter values according to the invention.

Such kit thus allows one to: measure the quantity of MCAM and the presence or absence and/or quantity of said one or more other biomarkers in the sample from the subject by respectively means (i) and (ii); establish (e.g., using means included in the kit or using suitable external means) a subject profile of the quantity of MCAM and the presence or absence and/or quantity of said one or more other biomarkers based on said measurements; compare the subject profile with the reference profile of (iv) or established by means (iv); find a deviation or no deviation of said subject profile from said reference profile; and consequently attribute said finding of deviation or no deviation to a particular prediction, diagnosis and/or prognosis of the conditions, symptoms and/or parameter values according to the invention in the subject.

In a further embodiment of the above kits, the means for measuring the quantity of MCAM and/or the presence or absence and/or quantity of the one or more other biomarkers may comprise, respectively, one or more binding agents capable of specifically binding to MCAM and/or to fragments thereof, and one or more binding agents capable of specifically binding to said one or more other biomarkers. In an embodiment, any one of said one or more binding agents may be an antibody, aptamer, photoaptamer, protein, peptide, peptidomimetic or a small molecule. In an embodiment, any one of said one or more binding agents may be advantageously immobilised on a solid phase or support.

In a further embodiment of the above kits, the means for measuring the quantity of MCAM and/or the presence or absence and/or quantity of the one or more other biomarkers may employ an immunoassay technology, such as direct ELISA, indirect ELISA, sandwich ELISA, competitive ELISA, multiplex ELISA, radioimmunoassay (RIA) or ELISPOT technologies, or may employ a mass spectrometry analysis technology or may employ a chromatography technology, or may employ a combination of said technologies.

An embodiment thus discloses a kit for predicting, diagnosing, prognosticating and/or monitoring the conditions, symptoms and/or parameter values according to the invention comprising:
(a) one or more binding agents capable of specifically binding to MCAM and/or to fragments thereof;
(b) preferably, a known quantity or concentration of MCAM and/or a fragment thereof (e.g., for use as controls, standards and/or calibrators);
(c) preferably, a reference value of the quantity of MCAM, or means for establishing said reference value.

Said components under (a) and/or (c) may be suitably labelled as taught elsewhere in this specification.

Another embodiment discloses a kit for predicting, diagnosing and/or prognosticating the conditions, symptoms and/or parameter values according to the invention comprising:
(a) one or more binding agents capable of specifically binding to MCAM and/or to fragments thereof;
(b) one or more binding agents capable of specifically binding to one or more other biomarkers;
(c) preferably, a known quantity or concentration of MCAM and/or a fragment thereof and a known quantity or concentration of said one or more other biomarkers (e.g., for use as controls, standards and/or calibrators);
(d) preferably, a reference profile of the quantity of MCAM and the presence or absence and/or quantity of said one or more other biomarkers, or means for establishing said reference profiles.

Said components under (a), (b) and/or (c) may be suitably labelled as taught elsewhere in this specification.

A further aspect relates to the use of the kit as described herein for diagnosing, predicting, prognosticating and/or monitoring the conditions, symptoms and/or parameter values according to the invention.

Also disclosed are reagents and tools useful for measuring MCAM and optionally the one or more other biomarkers concerned herein.

For example, a further aspect relates to a protein, polypeptide or peptide array or microarray comprising
(a) MCAM and/or a fragment thereof, preferably a known quantity or concentration of said MCAM and/or fragment thereof; and
(b) optionally and preferably, one or more other biomarkers, preferably a known quantity or concentration of said one or more other biomarkers.

Another aspect relates to a binding agent array or microarray comprising:
(a) one or more binding agents capable of specifically binding to MCAM and/or to fragments thereof, preferably a known quantity or concentration of said binding agents; and
(b) optionally and preferably, one or more binding agents capable of specifically binding to one or more other biomarkers, preferably a known quantity or concentration of said binding agents.

Also disclosed are kits as taught here above configured as portable devices, such as, for example, bed-side devices, for use at home or in clinical settings.

A related aspect thus provides a portable testing device capable of measuring the quantity of MCAM in a sample from a subject comprising:
(i) means for obtaining a sample from the subject,
(ii) means for measuring the quantity of MCAM in said sample, and
(iii) means for visualising the quantity of MCAM measured in the sample.

In an embodiment, the means of parts (ii) and (iii) may be the same, thus providing a portable testing device capable of measuring the quantity of MCAM in a sample from a subject comprising (i) means for obtaining a sample from the subject; and (ii) means for measuring the quantity of MCAM in said sample and visualising the quantity of MCAM measured in the sample.

In an embodiment, said visualising means is capable of indicating whether the quantity of MCAM in the sample is above or below a certain threshold level and/or whether the quantity of MCAM in the sample deviates or not from a reference value of the quantity of MCAM, said reference value representing a known prediction, diagnosis and/or prognosis of the conditions, symptoms and/or parameter values according to the invention. Hence, in an embodiment, the portable testing device may suitably also comprise said reference value or means for establishing said reference value.

In an embodiment, the threshold level is chosen such that the quantity of MCAM in the sample above or below (depending on the queried condition, symptom and/or parameter value) said threshold level indicates that the subject has or is at risk of having the conditions, symptoms and/or parameter values according to the invention or indicates a poor prognosis for such in the subject, and the quantity of MCAM in the sample below or above said threshold level, respectively, indicates that the subject does not have or is not at risk of having the conditions, symptoms and/or parameter values according to the invention or indicates a good prognosis for such in the subject.

In an embodiment, the portable testing device comprises a reference value representing the prediction or diagnosis of the absence of the conditions, symptoms and/or parameter values according to the invention or representing a good prognosis for such, or comprises means for establishing said reference value, and an elevated or reduced (depending on the queried condition, symptom and/or parameter value) quantity of MCAM in the sample from the subject compared to said reference value indicates that the subject has or is at risk of having the conditions, symptoms and/or parameter values according to the invention or indicates a poor prognosis for such in the subject.

In another embodiment, the portable testing device comprises a reference value representing the prediction or diagnosis of the conditions, symptoms and/or parameter values according to the invention or representing a poor prognosis for such, or comprises means for establishing said reference value, and a comparable quantity of MCAM in the sample from the subject compared to said reference value indicates that the subject has or is at risk of having the conditions, symptoms and/or parameter values according to the invention or indicates a poor prognosis for such in the subject.

In a further embodiment, the measuring (and optionally visualisation) means of the portable testing device may comprise a solid support having a proximal and distal end, comprising:
  a sample application zone in the vicinity of the proximal end;
  a reaction zone distal to the sample application zone; and
  a detection zone distal to the reaction zone;
  optionally control standards comprising MCAM protein or peptide fragments, whereby said support has a capillary property that directs a flow of fluid sample applied in the application zone in a direction from the proximal end to the distal end, and
  optionally comprising a fluid source improving the capillary flow of a more viscous sample.

In an embodiment, the reaction zone may comprise one or more bands of a MCAM-specific binding molecules conjugated to a detection agent, which MCAM specific binding molecule conjugate is disposed on the solid support such that it can migrate with the capillary flow of fluid; and wherein the detection zone comprises one or more capture bands comprising a population of MCAM specific molecule immobilised on the solid support.

In an embodiment, the reaction zone may additionally comprise one or more bands of capture MCAM-specific binding molecules in an amount sufficient to prevent a threshold quantity of MCAM specific binding molecule conjugates to migrate to the detection zone. In an alternative embodiment, said device additionally comprises means for comparing the amount of captured MCAM specific binding molecule conjugate with a threshold value.

In preferred embodiments of the kits and devices of the present invention, the MCAM protein detection is done in a plasma sample, implying that the circulating MCAM protein is detected, regardless of whether or not this circulating form corresponds to the soluble form or to a degradation product of the full-length or soluble form. In a preferred embodiment, the MCAM protein detected by said kits or devices is not membrane or cell-bound. Preferably the means for detecting said MCAM protein or fragment is capable of detecting both the full-length protein, mature protein or processed protein or the plasma circulating form thereof. More preferably, said means for detecting the MCAM protein is specifically recognising the plasma circulating from of MCAM as defined herein.

These and further aspects and preferred embodiments are described in the following sections and in the appended claims.

BRIEF DESCRIPTION OF FIGURES

FIG. 1 illustrates the protein sequence of the MCAM biomarker, taken from NP_006491 (SEQ ID NO.1). The protein is known as melanoma cell adhesion molecule (MCAM), or as MUC18 or CD146. The signal peptide and transmembrane and cytoplasmic domains are indicated in small caps. Also indicated is the selected MASSterclass quantified peptide (pept25—bold, underlined: SEQ ID NO.2). This MASSterclass peptide can quantify both the full length and cleaved soluble form of MCAM.

FIG. 3: Plan (A) and side view (B) of a test strip according to the invention.

FIG. 4: Plan view of a test cartridge according to the invention.

DETAILED DESCRIPTION OF THE INVENTION

Figure 2:
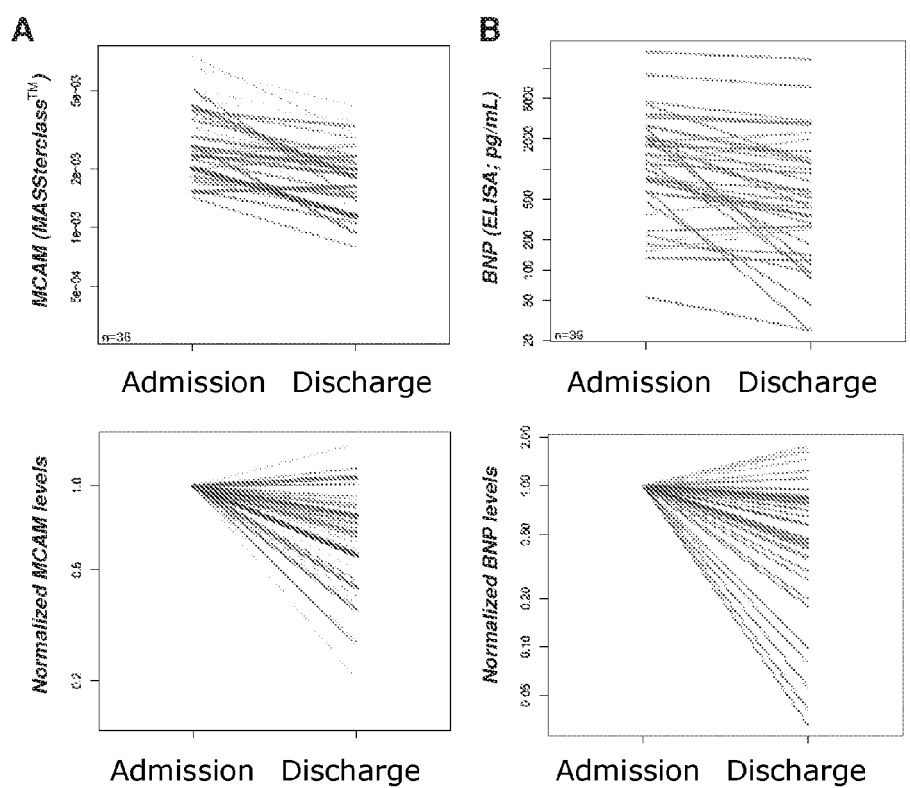
FIG. 2 illustrates the levels of MCAM (A) and BNP (B) measured in AHF patients at admission and in the same patients at discharge from hospital. The top plot shows the raw values as measured by MASSterclass or ELISA, while the bottom plot shows normalized values which are fold changes between admission and discharge.

As used herein, the singular forms "a", "an", and the include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps.

The recitation of numerical ranges by endpoints includes all numbers and fractions subsumed within the respective ranges, as well as the recited endpoints.

The term "about" as used herein when referring to a measurable value such as a parameter, an amount, a temporal duration, and the like, is meant to encompass variations of and from the specified value, in particular variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier "about" refers is itself also specifically, and preferably, disclosed.

All documents cited in the present specification are hereby incorporated by reference in their entirety.

Unless otherwise specified, all terms used in disclosing the invention, including technical and scientific terms, have the meaning as commonly understood by one of ordinary skill in the art to which this invention belongs. By means of further guidance, term definitions may be included to better appreciate the teaching of the present invention.

The present invention derives from the highly innovative realisation of the inventors that MCAM is a valuable biomarker particularly for fluid homeostasis, in particular homeostatic imbalance. The inventors have validated MCAM as a biomarker for several symptoms or parameters which are associated with fluid homeostasis, such as an increased fluid build-up, as measured by an increased vascular filling volume and weight gain, in particular edema; or on the other hand a decrease in body fluid, as measured by a decreased vascular filling volume and weight loss, in particular dehydration.

In addition, the inventors have validated MCAM as a biomarker for (acute) heart failure, in particular as a biomarker for specifically systolic dysfunction as an underlying cause of (acute) heart failure, including systolic dysfunction associated parameters such as ejection fraction (EF) and cardiac filling volume and pressure.

The term "biomarker" is widespread in the art and may broadly denote a biological molecule and/or a detectable portion thereof whose qualitative and/or quantitative evaluation in a subject is predictive or informative (e.g., predictive, diagnostic and/or prognostic) with respect to one or more aspects of the subject's phenotype and/or genotype, such as, for example, with respect to the status of the subject as to a given disease or condition.

The term "fluid homeostasis" as used herein carries its art-established meaning. By means of further guidance, the term "fluid homeostasis" relates to fluid or water homeostasis in a subject, wherein fluid or water content in a subject is kept constant or balanced by means of regulatory mechanisms including positive and negative feedback loops to increase or decrease fluid or water retention or secretion in response to changing internal (i.e. physiological) and/or external (i.e. environmental) conditions. Disturbance of fluid homeostasis leads to fluid homeostatic imbalance or impaired fluid homeostasis. Therefore "homeostatic imbalance" or "impaired homeostasis" as used herein refers to a deviation from (normal) homeostasis in respect of fluid household. As such, these terms refer to a situation wherein either too much fluid is present in a subject (i.e. a subject is over-filled), or in the alternative too little fluid is present in a subject (i.e. a subject is under-filled). Disorders of body water homeostasis can be divided into hypo-osmolar disorders, in which there is an excess of body water relative to body solute, and hyperosmolar disorders, in which there is a deficiency of body water relative to body solute. Hence, osmolarity measurements (e.g. electrolyte concentration) give an indication of fluid homeostasis. An impaired fluid homeostasis or a fluid homeostatic imbalance, according to the invention, relates to an altered vascular filling volume in said subject. An impaired fluid homeostasis or a fluid homeostatic imbalance, according to the invention, further relates to a situation wherein a subject presents itself with edema, or dehydration in the alternative. According to the invention, fluid homeostatic imbalance may be caused for example, but without limitation, by hyponatremia, such as isotonic hyponatremia, hypertonic hyponatremia, hypotonic hyponatremia, hypovolemic hypoosmolar hyponatremia, extrarenal solute losses, renal solute losses, euvolemic hypoosmolar hyponatremia, syndrome of inappropriate antidiuretic hormone secretion, glucocorticoid deficiency, hypothyroidism, hypervolemic hypoosmolar hyponatremia, congestive heart failure, cirrhosis, advanced renal failure, severe acute symptomatic hyponatremia, severe chronic symptomatic hyponatremia; hypernatremia, such as hypervolemic hypernatremia, hypodipsic hypernatremia, hypernatremia from increased water losses, central diabetes insipidus, nephrogenic diabetes insipidus.

The term "fluid build-up" as used herein means an increase in body fluid in a subject. As such, fluid build-up is associated with fluid retention. Fluid build-up can amongst others be caused for instance by (acute) heart failure, in particular due to systolic dysfunction, or kidney dysfunction or failure, in particular a dysfunction that prevents or otherwise interferes with normal secretion of fluids in a subject, such as nephrotic syndrome. Characteristics of fluid build-up include an increased vascular filling volume (or vascular volume expansion) and an increased vascular filling pressure. As used herein "filling status" or "fluid load" refers to the fluid content in a subject, in particular vascular, tissue and interstitial fluid content. As used herein "vascular filling volume" refers to the amount or volume of fluids in the vasculature. As used herein "vascular filling pressure" refers to the pressure which is generated by the amount or volume of fluids in the vasculature. As used herein the terms "vascular filling volume" and "vascular filling pressure" may be used interchangeably. Symptoms of fluid build-up in general and an increased vascular filling volume and/or pressure include edema. As used herein, "edema" refers to extravascular fluid build-up or retention, as caused by an increased vascular filling volume or pressure. According to the invention, fluid build-up, an increased vascular filling volume and/or pressure and edema may be caused by (acute) heart failure, systolic dysfunction, kidney dysfunction or any pathophysiological mechanism known in the art to cause such fluid imbalance or abnormal fluid homeostasis. As used herein, the term "weight gain" refers specifically to weight gain which is associated with fluid build-up and its associated parameters, including vascular filling volume and/or pressure, an increase of which may lead to or is correlated with edema. As used herein, "weight loss" likewise refers specifically to a decrease in fluids and its associated parameters, including vascular filling volume and/or pressure, a decrease of which may lead to or is correlated with dehydration.

As used herein, "kidney or renal dysfunction" or "kidney or renal failure" carries its respective art-established meanings. By means of further guidance, the term "kidney dysfunction" or "kidney failure" broadly refers to an impaired kidney function, in particular the filtering function of the kidney. As used herein, "kidney or renal failure" refers particularly to the inability of the kidneys to maintain fluid homeostasis. Causes for kidney failure include, but are not limited to, decreased blood supply to the kidney (such as hypovolemia or dehydration), medication (i.e. medicines which are toxic to the kidney), loss of blood supply to the kidney due to obstruction of the renal artery or vein, kidney insults or trauma, sepsis, rhabdomyolysis, multiple myeloma, acute or chronic glomerulonephritis or inflammation of the glomeruli, obstruction of the bladder or the ureters prostatic hypertrophy or prostate cancer, kidney stones, poorly controlled diabetes, poorly controlled high blood pressure, polycystic kidney disease, reflux nephropathy, . . . .

The terms "heart failure", "acute heart failure" and "chronic heart failure" as used herein carry their respective art-established meanings. By means of further guidance, the term "heart failure" as used herein broadly refers to pathological conditions characterised by an impaired diastolic or systolic blood flow rate and thus insufficient blood flow from the ventricle to peripheral organs.

"Acute heart failure" or also termed "acute decompensated heart failure" may be defined as the rapid onset of symptoms and signs secondary to abnormal cardiac function, resulting in the need for urgent therapy. AHF can present itself acute de novo (new onset of acute heart failure in a patient without previously known cardiac dysfunction) or as acute decompensation of CHF.

The cardiac dysfunction may be related to systolic or diastolic dysfunction, to abnormalities in cardiac rhythm, or to preload and afterload mismatch. It is often life threatening and requires urgent treatment. According to established classification, AHF includes several distinct clinical conditions of presenting patients: (I) acute decompensated congestive heart failure, (II) AHF with hypertension/hypertensive crisis, (III) AHF with pulmonary oedema, (IVa) cardiogenic shock/low output syndrome, (IVb) severe cardiogenic shock, (V) high output failure, and (VI) right-sided acute heart failure. For detailed clinical description, classification and diagnosis of AHF, and for summary of further AHF classification systems including the Killip classification, the Forrester classification and the 'clinical severity' classification, refer inter alia to Nieminen et al. 2005 ("Executive summary of the guidelines on the diagnosis and treatment of acute heart failure: the Task Force on Acute Heart Failure of the European Society of Cardiology". Eur Heart J 26: 384-416) and references therein.

The term "systolic dysfunction" as used herein carries its art-established meaning. By means of further guidance, the term "systolic dysfunction" can be used interchangeably with synonymous terms known to the skilled person, such as "systolic ventricular dysfunction or failure" or "systolic heart dysfunction or failure". Essentially, "systolic dysfunction" refers to a failure of the pump function of the heart due to a decreased contractility of the ventricle.

The term "diastolic dysfunction" as used herein carries its art-established meaning. By means of further guidance, the term "diastolic dysfunction" can be used interchangeably with synonymous terms known to the skilled person, such as "diastolic ventricular dysfunction or failure" or "diastolic heart dysfunction or failure". Essentially, "diastolic dysfunction" refers to a failure of the pump function of the heart due to impaired ventricular filling.

As used herein, the term "(left) ventricular ejection fraction" means the output of the (left) ventricle during systole, and represents the fraction of blood pumped out of a (left) ventricle with each heart beat. By definition, the volume of blood within a ventricle immediately before a contraction is known as the end-diastolic volume. Similarly, the volume of blood left in a ventricle at the end of contraction is end-systolic volume. The difference between end-diastolic and end-systolic volumes is the stroke volume, the volume of blood ejected with each beat. Ejection fraction (EF) is the fraction of the end-diastolic volume that is ejected with each beat; that is, it is stroke volume (SV) divided by end-diastolic volume (EDV): $EF=SV/EDV=(EDV-ESV)/EDV$.

As used herein, the term "cardiac filling pressure" relates to the pressure with which the ventricle is filled with blood. Cardiac filling pressures are monitored to estimate cardiac filling volumes, which, in turn, determine the stroke outputs of the left and right ventricles. As used herein, cardiac filling pressure is a representation of left ventricular end-diastolic pressure. Methods for determining or estimating cardiac filling pressure are known in the art and include ultrasound (echocardiography) and Doppler measurements as well as direct measurement through catherization of the ventricle. Cardiac filling pressure can be indirectly estimated through measurement of left atrial pressure, central venous pressure or pulmonary artery or capillary wedge pressure.

The term "chronic heart failure" (CHF) generally refers to a case of heart failure that progresses so slowly that various compensatory mechanisms work to bring the disease into equilibrium. Common clinical symptoms of CHF include inter alia any one or more of breathlessness, diminishing exercise capacity, fatigue, lethargy and peripheral oedema. Other less common symptoms include any one or more of palpitations, memory or sleep disturbance and confusion, and usually co-occur with one or more of the above recited common symptoms.

In studies such as the present one, CHF population may differ from the AHF population in that CHF patients do not have an acute decompensation and hence do not represent themselves to the ED at the time the clinical sample used in such a study or research is taken. Chronic heart failure patients may, however, easily decompensate leading to "acute heart failure".

In studies such as the present one, a population of dyspneic patients without heart failure may comprise for example patients who present themselves to the ED with similar symptoms as AHF population but where the cause of dyspnea is unrelated to acute decompensated heart failure. Typical examples are COPD or pneumonia patients. Such patients may or may not have underlying heart failure history, which may particularly complicate the final diagnosis using conventional diagnostic means such as BNP or NT-pro-BNP measurements.

The terms "predicting" or "prediction", "diagnosing" or "diagnosis" and "prognosticating" or "prognosis" are commonplace and well-understood in medical and clinical practice. By means of further explanation and without limitation, "predicting" or "prediction" generally refer to an advance declaration, indication or foretelling of a disease or condition in a subject not (yet) having said disease or condition. For example, a prediction of a disease or condition in a subject may indicate a probability, chance or risk that the subject will develop said disease or condition, for example within a certain time period or by a certain age. Said probability, chance or risk may be indicated inter alia as an absolute value, range or statistics, or may be indicated relative to a suitable control subject or subject population (such as, e.g., relative to a general, normal or healthy subject or subject population). Hence, the probability, chance or risk that a subject will develop a disease or condition may be advantageously indicated as increased or decreased, or as fold-increased or fold-decreased relative to a suitable control subject or subject population.

As used herein, the term "prediction of the conditions, symptoms and/or parameters according to the invention and as described herein", in particular fluid homeostatic imbalance, fluid build-up or fluid decrease, increased or decreased vascular filling volume and/or pressure, weight gain or loss, edema or dehydration, systolic dysfunction, (acute) heart failure, LVEF, LVEDP, cardiac filling pressure in a subject may also particularly mean that the subject has a 'positive' prediction of such, i.e., that the subject is at risk of having such (e.g., the risk is significantly increased vis-à-vis a control subject or subject population). The term "prediction of no conditions, symptoms and/or parameters according to the invention and as described herein" in a subject may particularly mean that the subject has a 'negative' prediction of such, i.e., that the subject's risk of having such is not significantly increased vis-à-vis a control subject or subject population.

The terms "diagnosing" or "diagnosis" generally refer to the process or act of recognising, deciding on or concluding on a disease or condition in a subject on the basis of symptoms and signs and/or from results of various diagnostic procedures (such as, for example, from knowing the presence, absence and/or quantity of one or more biomarkers characteristic of the diagnosed disease or condition).

As used herein, "diagnosis of the conditions, symptoms and/or abnormal parameter values according to the invention and as described herein", in particular fluid homeostatic imbalance, fluid build-up or fluid decrease, increased or decreased vascular filling volume and/or pressure, weight gain or loss, edema or dehydration, systolic dysfunction, (acute) heart failure, LVEF, LVEDP, cardiac filling pressure, in a subject may particularly mean that the subject has such, hence, is diagnosed as having such. "Diagnosis of no conditions, symptoms and/or abnormal parameter values according to the invention and as described herein, in particular fluid homeostatic imbalance, fluid build-up or fluid decrease, increased or decreased vascular filling volume and/or pressure, weight gain or loss, edema or dehydration, systolic dysfunction, (acute) heart failure, LVEF, LVEDP, cardiac filling pressure," in a subject may particularly mean that the subject does not have such, hence, is diagnosed as not having such. A subject may be diagnosed as taught herein as not having such despite displaying one or more conventional symptoms or signs reminiscent of such.

The terms "prognosticating" or "prognosis" generally refer to an anticipation on the progression of a disease or condition and the prospect (e.g., the probability, duration, and/or extent) of recovery.

A good prognosis of the conditions, symptoms and/or normalization of the parameters according to the invention and as described herein may generally encompass anticipation of a satisfactory partial or complete recovery from the conditions, symptoms and/or normalization of the parameters according to the invention and as described herein, preferably within an acceptable time period. A good prognosis of such may more commonly encompass anticipation of not further worsening or aggravating of such, preferably within a given time period.

A poor prognosis of the conditions, symptoms and/or normalization of the parameters according to the invention and as described herein may generally encompass anticipation of a substandard recovery and/or unsatisfactorily slow recovery, or to substantially no recovery or even further worsening of such.

The various aspects and embodiments taught herein may rely on measuring the quantity of MCAM, and optionally measuring the presence or absence and/or quantity of one or more other relevant biomarkers in a sample from a subject. In addition various clinical parameters associated with the conditions, symptoms and/or parameters as described herein according to the invention may be measured, such as glomerular filtration rate, urinary output, weight or any other clinical parameter known in the art to be associated with the conditions, symptoms and/or parameters as described. Combinations of the biomarkers and clinical parameters as taught herein are also contemplated.

The term "subject" or "patient" as used herein typically denotes humans, but may also encompass reference to non-human animals, preferably warm-blooded animals, more preferably mammals, such as, e.g., non-human primates, rodents, canines, felines, equines, ovines, porcines, and the like.

The terms "sample" or "biological sample" as used herein include any biological specimen obtained from a subject. Samples may include, without limitation, whole blood, plasma, serum, red blood cells, white blood cells (e.g., peripheral blood mononuclear cells), saliva, urine, stool (i.e., faeces), tears, sweat, sebum, nipple aspirate, ductal lavage, tumour exudates, synovial fluid, cerebrospinal fluid, lymph, fine needle aspirate, amniotic fluid, interstitial fluid, any other bodily fluid, cell lysates, cellular secretion products, inflammation fluid, semen and vaginal secretions. Preferred samples may include ones comprising MCAM in detectable quantities. In preferred embodiments, the sample may be whole blood or a fractional component thereof such as, e.g., plasma, serum, or a cell pellet. Preferably the sample is readily obtainable by minimally invasive methods. Samples may also include tissue samples and biopsies, tissue homogenates and the like. Preferably, the sample used to detect MCAM levels is blood plasma. The term "plasma" defines the colorless watery fluid of the blood that contains no cells, but in which the blood cells (erythrocytes, leukocytes, thrombocytes, etc.) are suspended, containing nutrients, sugars, proteins, minerals, enzymes, etc.

A molecule or analyte such as a protein, polypeptide or peptide, or a group of two or more molecules or analytes such as two or more proteins, polypeptides or peptides, is "measured" in a sample when the presence or absence and/or quantity of said molecule or analyte or of said group of molecules or analytes is detected or determined in the sample, preferably substantially to the exclusion of other molecules and analytes.

The terms "quantity", "amount" and "level" are synonymous and generally well-understood in the art. The terms as used herein may particularly refer to an absolute quantification of a molecule or an analyte in a sample, or to a relative quantification of a molecule or analyte in a sample, i.e., relative to another value such as relative to a reference value as taught herein, or to a range of values indicating a base-line expression of the biomarker. These values or ranges can be obtained from a single patient or from a group of patients.

An absolute quantity of a molecule or analyte in a sample may be advantageously expressed as weight or as molar amount, or more commonly as a concentration, e.g., weight per volume or mol per volume.

A relative quantity of a molecule or analyte in a sample may be advantageously expressed as an increase or decrease or as a fold-increase or fold-decrease relative to said another value, such as relative to a reference value as taught herein. Performing a relative comparison between first and second parameters (e.g., first and second quantities) may but need not require to first determine the absolute values of said first and second parameters. For example, a measurement method can produce quantifiable readouts (such as, e.g., signal intensities) for said first and second parameters, wherein said readouts are a function of the value of said parameters, and wherein said readouts can be directly compared to produce a relative value for the first parameter vs. the second parameter, without the actual need to first convert the readouts to absolute values of the respective parameters.

As used herein, the term "MCAM" corresponds to the protein commonly known as Melanoma Cell Adhesion Molecule (MCAM), MUC18 or CD146, i.e. the proteins and polypeptides commonly known under these designations in the art. The terms encompass such proteins and polypeptides of any organism where found, and particularly of animals, preferably vertebrates, more preferably mammals, including humans and non-human mammals, even more preferably of humans. The terms particularly encompass such proteins and polypeptides with a native sequence, i.e., ones of which the primary sequence is the same as that of MCAM found in or derived from nature. A skilled person understands that native sequences of MCAM may differ between different species due to genetic divergence between such species. Moreover, the native sequences of MCAM may differ between or within different individuals of the same species due to normal genetic diversity (variation) within a given species. Also, the native sequences of MCAM may differ between or even within different individuals of the same species due to post-transcriptional or post-translational modifications. Accordingly, all MCAM sequences found in or derived from nature are considered "native". The terms encompass MCAM proteins and polypeptides when forming a part of a living organism, organ, tissue or cell, when forming a part of a biological sample, as well as when at least partly isolated from such sources. The terms also encompass proteins and polypeptides when produced by recombinant or synthetic means.

Exemplary MCAM includes, without limitation, human MCAM having primary amino acid sequence as annotated under Uniprot/Swissprot (http://www.expasy.org/) accession number NP_006491 as shown in FIG. 1 (SEQ ID NO: 1). A skilled person can also appreciate that said sequences are of precursor of MCAM and may include parts which are processed away from mature MCAM. For example, the MCAM protein can be in a soluble form or can be attached to the cell membrane. In FIG. 1, the signal peptide and transmembrane and cytoplasmic domains are indicated in small caps in the amino acid sequence. Also indicated is the selected MASSterclass quantified peptide (pept25—bold, underlined: SEQ ID NO.2). This MASSterclass peptide can quantify both the full length and cleaved soluble form of MCAM, although due to the experimental set-up only the plasma circulating fraction (i.e. the non-cell bound fraction) is measured.

The MCAM protein is specific for endothelial cells and vascular smooth muscle cells and has been used as a tool for sorting endothelial cells out of a population of blood cells, based on the membrane bound form of CD146. MCAM belongs to the immunoglobulin supergene family with five immunoglobulin like domains (V-V-C2-C2-C2), a transmembrane region and a 63 residue cytoplasmic tail. It is a membrane glycoprotein that functions as a Ca2+ independent cell adhesion molecule involved in heterophilic cell to cell interactions. The protein has a molecular size of 130 kDa in its reduced form (118 kDa unreduced), and N linked glycosylation accounts for fifty percent of the apparent molecular weight. Soluble CD146 is released by ectodomain shedding (through the action of MMPs). Increased plasma levels of soluble CD146 was observed in patients with chronic renal failure (Healthy serum levels: ~270 ng/ml; renal failure patients: ~500 ng/ml) as discussed in Saito et al., 2008 (Clin Exp Nephrol. 2008 February; 12(1):58-64. Epub 2008 Jan. 5). On the other hand, decreased serum levels of sCD146 (soluble CD146) were observed in patients with Inflammatory Bowel Disease (IBD) such as Crohn's disease, while the membrane bound CD146 expression is increased in active IBD (Bardin et al., Inflamm. Bowel Dis. 2006 January; 12(1): 16-21 and Reumaux et al., Inflamm. Bowel Dis. 2007 October; 13(10):1315-7). The latter two publications indicate that there is a clear difference in correlation between the condition of the patient and the levels of 1) the soluble MCAM and 2) the cell- or membrane-bound form(s) of MCAM. In a preferred embodiment of the methods, kits and devices of present invention as defined herein, the circulating MCAM protein, e.g. the form circulating in the blood plasma, is detected, as opposed to the membrane- or cell-bound MCAM protein (e.g. MCAM present on the endothelial cell surface).

MCAM has been known as an endothelial cell injury marker, but has not been shown to be useful to evaluate fluid homeostasis, in particular homeostatic imbalance, or the associated symptoms or parameters; nor has it been shown to be correlated with systolic dysfunction or the associated symptoms or parameters. Furthermore, the MCAM marker is often used as a tool for sorting endothelial cells, implying the membrane bound (full-length) protein is used (cf. e.g. WO2006/020936).

The reference herein to MCAM may also encompass fragments of MCAM. Hence, the reference herein to measuring MCAM, or to measuring the quantity of MCAM, may encompass measuring the MCAM protein or polypeptide, such as, e.g., measuring the mature and/or the MMP-processed soluble form (shortly called "soluble form" hereinafter) of MCAM and/or measuring one or more fragments thereof. For example, MCAM and/or one or more fragments thereof may be measured collectively, such that the measured quantity corresponds to the sum amounts of the collectively measured species. In another example, MCAM and/or one or more fragments thereof may be measured each individually. Preferably, said fragment of MCAM is a plasma circulating form of MCAM.

The expression "plasma circulating form of MCAM" or shortly "circulating form" encompasses all MCAM proteins or fragments thereof that circulate in the plasma, i.e. are not cell- or membrane bound. Without wanting to be bound by any theory, such circulating forms can be derived from the full-length MCAM protein through natural processing (e.g. MMP-cleavage into its "soluble form" as indicated above), or can be resulting from known degradation processes occurring in said sample. In certain situations, the circulating form can also be the full-length MCAM protein, which is found to be circulating in the plasma. Said "circulating form" can thus be any MCAM protein or any processed soluble form of MCAM or fragments of either one, that is circulating in the sample, i.e. which is not bound to a cell- or membrane fraction of said sample.

As used herein, the terms atrial natriuretic peptide (ANP), pro-ANP and mid-regional portion of pro-ANP (MR-proANP) refer to peptides commonly known under these designations in the art. As further explanation and without limitation, in vivo mature ANP is derived from carboxyl terminal amino acids 99-126 of the 126-amino acid prohormone (proANP) known per se. Mid-regional proANP may particularly refer to about amino acids 53-90 of proANP.

As used herein, the terms "pro-B-type natriuretic peptide" (also abbreviated as "proBNP") and "amino terminal pro-B-type natriuretic peptide" (also abbreviated as "NTproBNP") and "B-type natriuretic peptide" (also abbreviated as "BNP") refer to peptides commonly known under these designations in the art. As further explanation and without limitation, in vivo proBNP, NTproBNP and BNP derive from natriuretic peptide precursor B preproprotein (preproBNP). In particular, proBNP peptide corresponds to the portion of preproBNP after removal of the N-terminal secretion signal (leader) sequence from preproBNP. NTproBNP corresponds to the N-terminal portion and BNP corresponds to the C-terminal portion of the proBNP peptide subsequent to cleavage of the latter C-terminally adjacent to amino acid 76 of proBNP.

As used herein, "Cystatin C" refers to a protein encoded by the CST3 gene, which is mainly used as a biomarker of kidney function. Alternative names include cystatin 3 (formerly gamma trace, post-gamma-globulin or neuroendocrine basic polypeptide). It is found in virtually all tissues and bodily fluids. It is a potent inhibitor of lysosomal proteinases (enzymes from a special subunit of the cell that break down proteins) and probably one of the most important extracellular inhibitors of cysteine proteases (it prevents the breakdown of proteins outside the cell by a specific type of protein degrading enzymes). Cystatin C belongs to the type 2 cystatin gene family.

As used herein, "neutrophil gelatinase-associated lipocalin" or "NGAL", also known as oncogenic lipocalin 24P3, uterocalin or lipocalin 2 (LCN2) refers to a 25-kD protein believed to bind small lipophilic substances such as bacteria-derived lipopolysaccharide (LPS) and formylpeptides and may function as a modulator of inflammation. NGAL can be used as a biomarker for kidney failure due to acute kidney injury.

As used herein, "U-albumin" refers to urinary albumin. As such, this term relates to the albumin concentration found in urine as a marker for kidney disease, in particular glomerular filtration defects.

As used herein, the term "y-glutamyl transpeptidase" or "gamma glutamyl transpeptidase" is used interchangeably with "gamma glutamyl transferase" (GGT). GGT is an enzyme that transfers gamma-glutamyl functional groups. GGT is present in the cell membranes of many tissues, including the kidneys, bile duct, pancreas, liver, spleen, heart, brain, and seminal vesicles. Urinary GGT can be used as a marker for renal ischemic injury.

As used herein, "N-Acetyl-beta-(D)-Glucosaminidase" or "NAG" refers to an enzyme involved in the hydrolysis of terminal N-acetyl-(D)-glucosamide residues in N-acetyl-β-(D)-glucosaminides. This enzyme belongs to the group of hexosaminidases. NAG is measured in urine as a non-invasive marker of renal damage and disease.

As used herein "alpha-1-microglobulin" or A1M, refers to a fragment of the alpha-1-microglobulin/bikunin precursor gene (AMBP). A1M belongs to the lipocalin superfamily. A1M is considered to be a marker of renal insufficiency, suggesting disturbed tubular function. A1M can be purified from the urine of patients with chronic renal tubular proteinuria.

As used herein "beta-2-microglobulin" or B2M refers to a serum protein found in association with the major histocompatibility complex (MHC) class I heavy chain on the surface of nearly all nucleated cells. In patients on long-term hemodialysis, it can aggregate into amyloid fibers that deposit in joint spaces, a disease known as dialysis-related amyloidosis. B2M serum and urinary concentrations are used to monitor glomerular and tubular nephropathies.

As used herein, "creatinine" refers to a break-down product of creatine phosphate in muscle, and is usually produced at a fairly constant rate by the body (depending on muscle mass). Chemically, creatinine is a spontaneously formed cyclic derivative of creatine. Creatinine is chiefly filtered out of the blood by the kidneys, though a small amount is actively secreted by the kidneys into the urine. There is little-to-no tubular reabsorption of creatinine. If the filtering of the kidney is deficient, blood levels rise. Therefore, creatinine levels in blood and urine may be used to calculate the creatinine clearance (CrCl), which reflects the glomerular filtration rate (GFR), as a measurement of renal function.

As used herein "vasopressin", also known as antidiuretic hormone (ADH), refers to a peptide hormone that controls the reabsorbtion of molecules in the tubules of the kidneys by affecting the tissue's permeability. It plays a key role in homeostasis, and the regulation of water, glucose, and salts in the blood. Vasopressin has three effects by which it contributes to increased urine osmolality (increased concentration) and decreased water excretion: increase in the permeability to water of the collecting duct cells in the kidney (i.e. antidiuresis); increase in the permeability of the inner medullary portion of the collecting duct to urea; and stimulation of sodium and chloride reabsorption. Decreased vasopressin release or decreased renal sensitivity to AVP leads to diabetes insipidus, a condition featuring hypernatremia, polyuria and polydipsia.

As used herein, "aldosteron" refers to a steroid hormone (mineralocorticoid family) produced by the outer-section (zona glomerulosa) of the adrenal cortex in the adrenal gland, and acts on the distal tubules and collecting ducts of the kidney to cause the conservation of sodium, secretion of potassium, increased water retention, and increased blood pressure. Aldosterone is a hormone that increases the reabsorption of sodium and water and the release (secretion) of potassium in the kidneys. This increases blood volume and, therefore, increases blood pressure. A measurement of aldosterone in blood may be termed a plasma aldosterone concentration (PAC), which may be compared to plasma renin activity (PRA) as a PAC/PRA ratio.

As used herein, "angiotensin" refers to an oligopeptide in the blood that causes vasoconstriction, increased blood pressure, and release of aldosterone from the adrenal cortex. It is a hormone and a powerful dipsogen. It is derived from the precursor molecule angiotensinogen, a serum globulin produced in the liver. It is part of the renin-angiotensin system, which is a major target for drugs that lower blood pressure. Angiotensin I is formed by the action of renin on angiotensinogen. It appears to have no biological activity and exists solely as a precursor to angiotensin II. Angiotensin I is converted to angiotensin II through removal of two C-terminal residues by the enzyme angiotensin-converting enzyme (ACE). Angiotensin II has a direct effect on the proximal tubules to increase sodium reabsorption. As used herein, "angiotensin converting enzyme" or "ACE" refers to an exopeptidase that is a circulating enzyme that participates in the body's renin-angiotensin system (RAS), which mediates extracellular volume (i.e. that of the blood plasma, lymph and interstitial fluid), and arterial vasoconstriction. It is secreted by pulmonary and renal endothelial cells and catalyzes the conversion of decapeptide angiotensin I to octapeptide angiotensin II. In addition, ACE degrades bradykinin, a potent vasodilator, and other vasoactive peptides.

The designations ANP, proANP, MR-proANP, proBNP, NTproBNP, BNP, Cystatin C, neutrophil gelatinase-associated lipocalin (NGAL), U-Albumin, y-glutamyl transpeptidase (γ-GT), N-Acetyl-beta-(D)-Glucosaminidase (NAG), alpha-1-microglobulin (A1M), beta-2-microglobulin (B2M), urea, creatinine, vasopression, aldosteron, angiotensin and ACE (hereafter referred to as "additional biomarkers") as used herein particularly refer to such peptides with a native sequence, i.e., peptides of which the primary sequence is the same as that of respectively ANP, proANP, MR-proANP, proBNP, NTproBNP, Cystatin C, neutrophil gelatinase-associated lipocalin (NGAL), U-Albumin, y-glutamyl transpeptidase (γ-GT), N-Acetyl-beta-(D)-Glucosaminidase (NAG), alpha-1-microglobulin (A1M), beta-2-microglobulin (B2M), urea, creatinine, vasopression, aldosteron, angiotensin, ACE BNP found in or derived from nature. A skilled person understands that native sequences of these additional biomarkers may differ between different species due to genetic divergence between such species. Moreover, the native sequences of these additional biomarkers may differ between or even within different individuals of the same species due to normal genetic diversity (variation) within a given species. Also, the native sequences of these additional biomarkers may differ between or even within different individuals of the same species due to post-transcriptional or post-translational modifications. Accordingly, all these additional biomarkers sequences found in or derived from nature are considered "native". The terms encompass such peptides from any organism where found, and particularly from animals, preferably vertebrates, more preferably mammals, including humans and non-human mammals, even more preferably from humans The designations these additional biomarkers as used herein encompass the respective peptides when forming a part of a living organism, organ, tissue or cell, when forming a part of a biological sample, as well as when at least partly isolated from such sources. The terms also encompass the respective peptides when produced by recombinant or synthetic means.

The reference herein to these additional biomarkers may also encompass fragments of any one of these additional biomarkers. Hence, the reference herein to measuring the presence or absence and/or quantity of these additional biomarkers, may encompass measuring peptides of these additional biomarkers and/or measuring one or more fragments of any one of these additional biomarker peptides. For example, these additional biomarker peptides and/or one or more fragments of any one thereof may be measured collectively, such that the measured quantity corresponds to the sum amount of the collectively measured species. In another example, these additional biomarker peptides and/or one or more fragments of any one thereof may be measured each individually.

Further, unless otherwise apparent from the context, reference herein to any protein, polypeptide or peptide and fragments thereof may generally also encompass modified forms of said protein, polypeptide or peptide and fragments such as bearing post-expression modifications including, for example, phosphorylation, glycosylation, lipidation, methylation, cysteinylation, sulphonation, glutathionylation, acetylation, oxidation of methionine to methionine sulphoxide or methionine sulphone, and the like.

In an embodiment, MCAM and fragments thereof, or the additional biomarkers as described herein and fragments thereof may be human, i.e., their primary sequence may be the same as a corresponding primary sequence of or present in a naturally occurring human MCAM and fragments thereof, or said biomarkers as described herein and fragments thereof. Hence, the qualifier "human" in this connection relates to the primary sequence of the respective proteins, polypeptides, peptides or fragments, rather than to their origin or source. For example, such proteins, polypeptides, peptides or fragments may be present in or isolated from samples of human subjects or may be obtained by other means (e.g., by recombinant expression, cell-free translation or non-biological peptide synthesis).

The term "fragment" of a protein, polypeptide or peptide generally refers to N-terminally and/or C-terminally deleted or truncated forms of said protein, polypeptide or peptide. The term encompasses fragments arising by any mechanism, such as, without limitation, by alternative translation, exo- and/or endo-proteolysis and/or degradation of said protein or polypeptide, such as, for example, in vivo or in vitro such as, for example, by physical, chemical and/or enzymatic proteolysis. Without limitation, a fragment of a protein, polypeptide or peptide may represent at least about 5%, or at least about 10%, e.g., ≥20%, ≥30% or ≥40%, such as ≥50%, e.g., ≥60%, ≥70% or ≥80%, or even ≥90% or ≥95% of the amino acid sequence of said protein, polypeptide or peptide.

For example, a fragment of MCAM may include a sequence of ≥5 consecutive amino acids, or ≥10 consecutive amino acids, or ≥20 consecutive amino acids, or ≥30 consecutive amino acids, e.g., ≥40 consecutive amino acids, such as for example ≥50 consecutive amino acids, e.g., ≥60, ≥70, ≥80, ≥90, ≥100, ≥200, ≥300, ≥400, ≥500 or ≥600 consecutive amino acids of MCAM.

In an embodiment, a fragment of MCAM may be N-terminally and/or C-terminally truncated by between 1 and about 20 amino acids, such as, e.g., by between 1 and about 15 amino acids, or by between 1 and about 10 amino acids, or by between 1 and about 5 amino acids, compared to mature, full-length MCAM (SEQ ID NO.1) or its soluble form (cf. FIG. 1).

In an embodiment, a fragment of ANP, proANP, MR-proANP, proBNP, NTproBNP, BNP, Cystatin C, NGAL, U-Albumin, γ-GT, NAG, A1M, B1M, creatinine, vasopressin, aldosteron, angiotensin, ACE may be N-terminally and/or C-terminally truncated by between 1 and about 20 amino acids, such as, e.g., by between 1 and about 15 amino acids, or by between 1 and about 10 amino acids, or by between 1 and about 5 amino acids, compared to ANP, proANP, MR-proANP, proBNP, NTproBNP, BNP, Cystatin C, NGAL, U-Albumin, γ-GT, NAG, A1M, B1M, creatinine, vasopressin, aldosteron, angiotensin, ACE. By means of example, proBNP, NTproBNP and BNP fragments useful as biomarkers are disclosed in WO 2004/094460.

In an embodiment, fragments of a given protein, polypeptide or peptide may be achieved by in vitro proteolysis of said protein, polypeptide or peptide to obtain advantageously detectable peptide(s) from a sample.

For example, such proteolysis may be effected by suitable physical, chemical and/or enzymatic agents, e.g., proteinases, preferably endoproteinases, i.e., protease cleaving internally within a protein, polypeptide or peptide chain. A non-limiting list of suitable endoproteinases includes serine proteinases (EC 3.4.21), threonine proteinases (EC 3.4.25), cysteine proteinases (EC 3.4.22), aspartic acid proteinases (EC 3.4.23), metalloproteinases (EC 3.4.24) and glutamic acid proteinases.

Exemplary non-limiting endoproteinases include trypsin, chymotrypsin, elastase, *Lysobacter enzymogenes* endoproteinase Lys-C, *Staphylococcus aureus* endoproteinase Glu-C (endopeptidase V8) or *Clostridium histolyticum* endoproteinase Arg-C (clostripain). Further known or yet to be identified enzymes may be used; a skilled person can choose suitable protease(s) on the basis of their cleavage specificity and frequency to achieve desired peptide forms.

Preferably, the proteolysis may be effected by endopeptidases of the trypsin type (EC 3.4.21.4), preferably trypsin, such as, without limitation, preparations of trypsin from bovine pancreas, human pancreas, porcine pancreas, recombinant trypsin, Lys-acetylated trypsin, trypsin in solution, trypsin immobilised to a solid support, etc. Trypsin is particularly useful, inter alia due to high specificity and efficiency of cleavage. The invention also contemplates the use of any trypsin-like protease, i.e., with a similar specificity to that of trypsin.

Otherwise, chemical reagents may be used for proteolysis. For example, CNBr can cleave at Met; BNPS-skatole can cleave at Trp.

The conditions for treatment, e.g., protein concentration, enzyme or chemical reagent concentration, pH, buffer, temperature, time, can be determined by the skilled person depending on the enzyme or chemical reagent employed.

Hence, in an aspect the invention also provides an isolated fragment of MCAM as defined here above. Such fragments may give useful information about the presence and quantity of MCAM in biological samples, whereby the detection of said fragments is of interest. Hence, the herein disclosed fragments of MCAM are useful biomarkers.

The term "isolated" with reference to a particular component (such as for instance, a protein, polypeptide, peptide or fragment thereof) generally denotes that such component exists in separation from—for example, has been separated from or prepared in separation from—one or more other components of its natural environment. For instance, an isolated human or animal protein, polypeptide, peptide or fragment exists in separation from a human or animal body where it occurs naturally.

The term "isolated" as used herein may preferably also encompass the qualifier "purified". As used herein, the term "purified" with reference to protein(s), polypeptide(s), peptide(s) and/or fragment(s) thereof does not require absolute purity. Instead, it denotes that such protein(s), polypeptide(s), peptide(s) and/or fragment(s) is (are) in a discrete environment in which their abundance (conveniently expressed in terms of mass or weight or concentration) relative to other proteins is greater than in a biological sample. A discrete environment denotes a single medium, such as for example a single solution, gel, precipitate, lyophilisate, etc. Purified peptides, polypeptides or fragments may be obtained by known methods including, for example, laboratory or recombinant synthesis, chromatography, preparative electrophoresis, centrifugation, precipitation, affinity purification, etc.

Purified protein(s), polypeptide(s), peptide(s) and/or fragment(s) may preferably constitute by weight ≥10%, more preferably ≥50%, such as ≥60%, yet more preferably ≥70%, such as ≥80%, and still more preferably ≥90%, such as ≥95%, ≥96%, ≥97%, ≥98%, ≥99% or even 100%, of the protein content of the discrete environment. Protein content may be determined, e.g., by the Lowry method (Lowry et al. 1951. J Biol Chem 193: 265), optionally as described by Hartree 1972 (Anal Biochem 48: 422-427). Also, purity of peptides or polypeptides may be determined by SDS-PAGE under reducing or non-reducing conditions using Coomassie blue or, preferably, silver stain.

A further embodiment provides isolated MCAM or fragments of MCAM as taught herein comprising a detectable label. This facilitates ready detection of such fragments. The term "label" as used throughout this specification refers to any atom, molecule, moiety or biomolecule that can be used to provide a detectable and preferably quantifiable read-out or property, and that can be attached to or made part of an entity of interest, such as a peptide or polypeptide or a specific-binding agent. Labels may be suitably detectable by mass spectrometric, spectroscopic, optical, colorimetric, magnetic, photochemical, biochemical, immunochemical or chemical means. Labels include without limitation dyes; radiolabels such as $^{32}P$, $^{33}P$, $^{35}S$, $^{125}I$, $^{131}I$; electron-dense reagents; enzymes (e.g., horse-radish peroxidase or alkaline phosphatase as commonly used in immunoassays); binding moieties such as biotin-streptavidin; haptens such as digoxigenin; luminogenic, phosphorescent or fluorogenic moieties; mass tags; and fluorescent dyes alone or in combination with moieties that can suppress or shift emission spectra by fluorescence resonance energy transfer (FRET).

In an embodiment, the isolated MCAM or fragments of MCAM as taught herein may be labelled by a mass-altering label. Preferably, a mass-altering label may involve the presence of a distinct stable isotope in one or more amino acids of the peptide vis-à-vis its corresponding non-labelled peptide. Mass-labelled peptides are particularly useful as positive controls, standards and calibrators in mass spectrometry applications. In particular, peptides including one or more distinct isotopes are chemically alike, separate chromatographically and electrophoretically in the same manner and also ionise and fragment in the same way. However, in a suitable mass analyser such peptides and optionally select fragmentation ions thereof will display distinguishable m/z ratios and can thus be discriminated. Examples of pairs of distinguishable stable isotopes include H and D, $^{12}C$ and $^{13}O$, $^{14}N$ and $^{15}N$ or $^{16}O$ and $^{18}O$. Usually, peptides and proteins of biological samples analysed in the present invention may substantially only contain common isotopes having high prevalence in nature, such as for example H, $^{12}C$, $^{14}N$ and $^{16}O$. In such case, the mass-labelled peptide may be labelled with one or more uncommon isotopes having low prevalence in nature, such as for instance D, $^{13}C$, $^{15}N$ and/or $^{18}O$. It is also conceivable that in cases where the peptides or proteins of a biological sample would include one or more uncommon isotopes, the mass-labelled peptide may comprise the respective common isotope(s).

Isotopically-labelled synthetic peptides may be obtained inter alia by synthesising or recombinantly producing such peptides using one or more isotopically-labelled amino acid substrates, or by chemically or enzymatically modifying unlabelled peptides to introduce thereto one or more distinct isotopes. By means of example and not limitation, D-labelled peptides may be synthesised or recombinantly produced in the presence of commercially available deuterated L-methionine $CH_3$—S—$CD_2CD_2$-CH($NH_2$)—COOH or deuterated arginine $H_2NC(=NH)$—NH—$(CD_2)_3$-CD($NH_2$)—COOH. It shall be appreciated that any amino acid of which deuterated or $^{15}N$- or $^{13}C$-containing forms exist may be considered for synthesis or recombinant production of labelled peptides. In another non-limiting example, a peptide may be treated with trypsin in $H_2^{16}O$ or $H_2^{18}O$, leading to incorporation of two oxygens ($^{16}O$ or $^{18}O$, respectively) at the COOH-termini of said peptide (e.g., US 2006/105415).

Accordingly, also contemplated is the use of MCAM and isolated fragments of MCAM as taught herein, optionally comprising a detectable label, as (positive) controls, standards or calibrators in qualitative or quantitative detection assays (measurement methods) of MCAM, and particularly in such methods for predicting, diagnosing, prognosticating and/or monitoring the conditions, symptoms and/or parameters in subjects as taught herein. The proteins, polypeptides or peptides may be supplied in any form, inter alia as precipitate, vacuum-dried, lyophilisate, in solution as liquid or frozen, or covalently or non-covalently immobilised on solid phase, such as for example, on solid chromatographic matrix or on glass or plastic or other suitable surfaces (e.g., as a part of peptide arrays and microarrays). The peptides may be readily prepared, for example, isolated from natural sources, or prepared recombinantly or synthetically.

Also provided are binding agents capable of specifically binding to any one or more of the isolated fragments of MCAM as taught herein. Further provided are binding agents capable of specifically binding to only one of the isolated fragments of MCAM as taught herein. Such binding agents may include inter alia an antibody, aptamer, photoaptamer, protein, peptide, peptidomimetic or a small molecule.

In a preferred embodiment, said binding agent is capable of binding both the membrane-bound and plasma circulating forms of MCAM. Preferably, said binding agent is capable of specifically binding or detecting the plasma circulating form of MCAM.

The term "specifically bind" as used throughout this specification means that an agent (denoted herein also as "specific-binding agent") binds to one or more desired molecules or analytes, such as to one or more proteins, polypeptides or peptides of interest or fragments thereof substantially to the exclusion of other molecules which are random or unrelated, and optionally substantially to the exclusion of other molecules that are structurally related.

The term "specifically bind" does not necessarily require that an agent binds exclusively to its intended target(s). For example, an agent may be said to specifically bind to protein(s) polypeptide(s), peptide(s) and/or fragment(s) thereof of interest if its affinity for such intended target(s) under the conditions of binding is at least about 2-fold greater, preferably at least about 5-fold greater, more preferably at least about 10-fold greater, yet more preferably at least about 25-fold greater, still more preferably at least about 50-fold greater, and even more preferably at least about 100-fold or more greater, than its affinity for a non-target molecule.

Preferably, the agent may bind to its intended target(s) with affinity constant ($K_A$) of such binding $K_A \geq 1 \times 10^6$ M$^{-1}$, more preferably $K_A \geq 1 \times 10^7$ M$^{-1}$, yet more preferably $K_A \geq 1 \times 10^8$ M$^{-1}$, even more preferably $K_A \geq 1 \times 10^9$ M$^{-1}$, and still more preferably $K_A \geq 1 \times 10^{10}$ M$^{-1}$ or $K_A \geq 1 \times 10^{11}$ M$^{-1}$, wherein $K_A$=[SBA_T]/[SBA][T], SBA denotes the specific-binding agent, T denotes the intended target. Determination of $K_A$ can be carried out by methods known in the art, such as for example, using equilibrium dialysis and Scatchard plot analysis.

Specific binding agents as used throughout this specification may include inter alia an antibody, aptamer, photoaptamer, protein, peptide, peptidomimetic or a small molecule.

As used herein, the term "antibody" is used in its broadest sense and generally refers to any immunologic binding agent. The term specifically encompasses intact monoclonal antibodies, polyclonal antibodies, multivalent (e.g., 2-, 3- or more-valent) and/or multi-specific antibodies (e.g., bi- or more-specific antibodies) formed from at least two intact antibodies, and antibody fragments insofar they exhibit the desired biological activity (particularly, ability to specifically bind an antigen of interest), as well as multivalent and/or multi-specific composites of such fragments. The term "antibody" is not only inclusive of antibodies generated by methods comprising immunisation, but also includes any polypeptide, e.g., a recombinantly expressed polypeptide, which is made to encompass at least one complementarity-determining region (CDR) capable of specifically binding to an epitope on an antigen of interest. Hence, the term applies to such molecules regardless whether they are produced in vitro or in vivo.

In an embodiment, an antibody may be any of IgA, IgD, IgE, IgG and IgM classes, and preferably IgG class antibody.

In an embodiment, the antibody may be a polyclonal antibody, e.g., an antiserum or immunoglobulins purified there from (e.g., affinity-purified).

In another preferred embodiment, the antibody may be a monoclonal antibody or a mixture of monoclonal antibodies. Monoclonal antibodies can target a particular antigen or a particular epitope within an antigen with greater selectivity and reproducibility.

By means of example and not limitation, monoclonal antibodies may be made by the hybridoma method first described by Kohler et al. 1975 (Nature 256: 495), or may be made by recombinant DNA methods (e.g., as in U.S. Pat. No. 4,816,567). Monoclonal antibodies may also be isolated from phage antibody libraries using techniques as described by Clackson et al. 1991 (Nature 352: 624-628) and Marks et al. 1991 (J Mol Biol 222: 581-597), for example.

In further embodiments, the antibody binding agents may be antibody fragments. "Antibody fragments" comprise a portion of an intact antibody, comprising the antigen-binding or variable region thereof. Examples of antibody fragments include Fab, Fab', F(ab')2, Fv and scFv fragments; diabodies; linear antibodies; single-chain antibody molecules; and multivalent and/or multispecific antibodies formed from antibody fragment(s), e.g., dibodies, tribodies, and multibodies. The above designations Fab, Fab', F(ab')2, Fv, scFv etc. are intended to have their art-established meaning.

The term antibody includes antibodies originating from or comprising one or more portions derived from any animal species, preferably vertebrate species, including, e.g., birds and mammals. Without limitation, the antibodies may be chicken, turkey, goose, duck, guinea fowl, quail or pheasant. Also without limitation, the antibodies may be human, murine (e.g., mouse, rat, etc.), donkey, rabbit, goat, sheep, guinea pig, camel (e.g., *Camelus bactrianus* and *Camelus dromaderius*), llama (e.g., *Lama paccos, Lama glama* or *Lama vicugna*) or horse.

A skilled person will understand that an antibody can include one or more amino acid deletions, additions and/or substitutions (e.g., conservative substitutions), insofar such alterations preserve its binding of the respective antigen. An antibody may also include one or more native or artificial modifications of its constituent amino acid residues (e.g., glycosylation, etc.).

Methods of producing polyclonal and monoclonal antibodies as well as fragments thereof are well known in the art, as are methods to produce recombinant antibodies or fragments thereof (see for example, Harlow and Lane, "Antibodies: A Laboratory Manual", Cold Spring Harbour Laboratory, New York, 1988; Harlow and Lane, "Using Antibodies: A Laboratory Manual", Cold Spring Harbour Laboratory, New York, 1999, ISBN 0879695447; "Monoclonal Antibodies: A Manual of Techniques", by Zola, ed., CRC Press 1987, ISBN 0849364760; "Monoclonal Antibodies: A Practical Approach", by Dean & Shepherd, eds., Oxford University Press 2000, ISBN 0199637229; Methods in Molecular Biology, vol. 248: "Antibody Engineering: Methods and Protocols", Lo, ed., Humana Press 2004, ISBN 1588290921).

The term "aptamer" refers to single-stranded or double-stranded oligo-DNA, oligo-RNA or oligo-DNA/RNA or any analogue thereof, that can specifically bind to a target molecule such as a peptide. Advantageously, aptamers can display fairly high specificity and affinity (e.g., $K_A$ in the order $1 \times 10^9$ M$^{-1}$) for their targets. Aptamer production is described inter alia in U.S. Pat. No. 5,270,163; Ellington & Szostak 1990 (Nature 346: 818-822); Tuerk & Gold 1990 (Science 249: 505-510); or "The Aptamer Handbook: Functional Oligonucleotides and Their Applications", by Klussmann, ed., Wiley-VCH 2006, ISBN 3527310592, incorporated by reference herein. The term "photoaptamer" refers to an aptamer that contains one or more photoreactive functional groups that can covalently bind to or crosslink with a target molecule. The term "peptidomimetic" refers to a non-peptide agent that is a topological analogue of a corresponding peptide. Methods of rationally designing peptidomimetics of peptides are known in the art. For example, the rational design of three peptidomimetics based on the sulphated 8-mer peptide CCK26-33, and of two peptidomimetics based on the 11-mer peptide Substance P, and related peptidomimetic design principles, are described in Horwell 1995 (Trends Biotechnol 13: 132-134).

The term "small molecule" refers to compounds, preferably organic compounds, with a size comparable to those organic molecules generally used in pharmaceuticals. The term excludes biological macromolecules (e.g., proteins, nucleic acids, etc.). Preferred small organic molecules range in size up to about 5000 Da, e.g., up to about 4000, preferably up to 3000 Da, more preferably up to 2000 Da, even more preferably up to about 1000 Da, e.g., up to about 900, 800, 700, 600 or up to about 500 Da.

Also provided are methods for immunising animals, e.g., non-human animals such as laboratory or farm, animals using (i.e., using as the immunising antigen) the herein taught fragments of MCAM, optionally attached to a presenting carrier. Immunisation and preparation of antibody reagents from immune sera is well-known per se and described in documents referred to elsewhere in this specification. The animals to be immunised may include any animal species, preferably warm-blooded species, more preferably vertebrate species, including, e.g., birds and mammals. Without limitation, the antibodies may be chicken, turkey, goose, duck, guinea fowl, quail or pheasant. Also without limitation, the antibodies may be human, murine (e.g., mouse, rat, etc.), donkey, rabbit, goat, sheep, guinea pig, camel, llama or horse.

The term "presenting carrier" or "carrier" generally denotes an immunogenic molecule which, when bound to a second molecule, augments immune responses to the latter, usually through the provision of additional T cell epitopes. The presenting carrier may be a (poly)peptidic structure or a non-peptidic structure, such as inter alia glycans, polyethylene glycols, peptide mimetics, synthetic polymers, etc. Exemplary non-limiting carriers include human Hepatitis B virus core protein, multiple C3d domains, tetanus toxin fragment C or yeast Ty particles.

Immune sera obtained or obtainable by immunisation as taught herein may be particularly useful for generating antibody reagents that specifically bind to one or more of the herein disclosed fragments of MCAM.

The invention also teaches a method for selecting specific-binding agents which bind (a) one or more of the MCAM fragments taught herein, substantially to the exclusion of (b) MCAM and/or other fragments thereof. Conveniently, such methods may be based on subtracting or removing binding agents which cross-react or cross-bind the non-desired MCAM molecules under (b). Such subtraction may be readily performed as known in the art by a variety of affinity separation methods, such as affinity chromatography, affinity solid phase extraction, affinity magnetic extraction, etc.

Any existing, available or conventional separation, detection and quantification methods can be used herein to measure the presence or absence (e.g., readout being present vs. absent; or detectable amount vs. undetectable amount) and/or quantity (e.g., readout being an absolute or relative quantity, such as, for example, absolute or relative concentration) of MCAM and/or fragments thereof and optionally of the one or more biomarkers useful for the conditions, symptoms and/or parameters according to the invention in samples (any molecules or analytes of interest to be so-measured in samples, including MCAM and fragments thereof, may be herein below referred to collectively as biomarkers).

For example, such methods may include immunoassay methods, mass spectrometry analysis methods, or chromatography methods, or combinations thereof.

The term "immunoassay" generally refers to methods known as such for detecting one or more molecules or analytes of interest in a sample, wherein specificity of an immunoassay for the molecule(s) or analyte(s) of interest is conferred by specific binding between a specific-binding agent, commonly an antibody, and the molecule(s) or analyte(s) of interest.

Immunoassay technologies include without limitation direct ELISA (enzyme-linked immunosorbent assay), indirect ELISA, sandwich ELISA, competitive ELISA, multiplex ELISA, radioimmunoassay (RIA), ELISPOT technologies, and other similar techniques known in the art. Principles of these immunoassay methods are known in the art, for example John R. Crowther, "The ELISA Guidebook", 1st ed., Humana Press 2000, ISBN 0896037282.

By means of further explanation and not limitation, direct ELISA employs a labelled primary antibody to bind to and thereby quantify target antigen in a sample immobilised on a solid support such as a microwell plate. Indirect ELISA uses a non-labelled primary antibody which binds to the target antigen and a secondary labelled antibody that recognises and allows to quantify the antigen-bound primary antibody. In sandwich ELISA the target antigen is captured from a sample using an immobilised 'capture' antibody which binds to one antigenic site within the antigen, and subsequent to removal of non-bound analytes the so-captured antigen is detected using a 'detection' antibody which binds to another antigenic site within said antigen, where the detection antibody may be directly labelled or indirectly detectable as above. Competitive ELISA uses a labelled 'competitor' that may either be the primary antibody or the target antigen. In an example, non-labelled immobilised primary antibody is incubated with a sample, this reaction is allowed to reach equilibrium, and then labelled target antigen is added. The latter will bind to the primary antibody wherever its binding sites are not yet occupied by non-labelled target antigen from the sample. Thus, the detected amount of bound labelled antigen inversely correlates with the amount of non-labelled antigen in the sample. Multiplex ELISA allows simultaneous detection of two or more analytes within a single compartment (e.g., microplate well) usually at a plurality of array addresses (see, for example, Nielsen & Geierstanger 2004. J Immunol Methods 290: 107-20 and Ling et al. 2007. Expert Rev Mol Diagn 7: 87-98 for further guidance). As appreciated, labelling in ELISA technologies and more generally in immunoassay technologies is usually by enzyme (such as, e.g., horse-radish peroxidase) conjugation and the end-point is typically colorimetric, chemiluminescent or fluorescent, magnetic, piezo electric, pyroelectric and other.

Radioimmunoassay (RIA) is a competition-based technique and involves mixing known quantities of radioactively-labelled (e.g., $^{125}$I- or $^{131}$I-labelled) target antigen with antibody to said antigen, then adding non-labelled or 'cold' antigen from a sample and measuring the amount of labelled antigen displaced (see, e.g., "An Introduction to Radioimmunoassay and Related Techniques", by Chard T, ed., Elsevier Science 1995, ISBN 0444821198 for guidance).

Further, mass spectrometry methods are suitable for measuring biomarkers.

Generally, any mass spectrometric (MS) techniques that can obtain precise information on the mass of peptides, and preferably also on fragmentation and/or (partial) amino acid sequence of selected peptides (e.g., in tandem mass spectrometry, MS/MS; or in post source decay, TOF MS), are useful herein. Suitable peptide MS and MS/MS techniques and systems are well-known per se (see, e.g., Methods in Molecular Biology, vol. 146: "Mass Spectrometry of Proteins and Peptides", by Chapman, ed., Humana Press 2000, ISBN 089603609x; Biemann 1990. Methods Enzymol 193: 455-

79; or Methods in Enzymology, vol. 402: "Biological Mass Spectrometry", by Burlingame, ed., Academic Press 2005, ISBN 9780121828073) and may be used herein.

MS arrangements, instruments and systems suitable for biomarker peptide analysis may include, without limitation, matrix-assisted laser desorption/ionisation time-of-flight (MALDI-TOF) MS; MALDI-TOF post-source-decay (PSD); MALDI-TOF/TOF; surface-enhanced laser desorption/ionization time-of-flight mass spectrometry (SELDI-TOF) MS; electrospray ionization mass spectrometry (ESI-MS); ESI-MS/MS; ESI-MS/(MS)$^n$ (n is an integer greater than zero); ESI 3D or linear (2D) ion trap MS; ESI triple quadrupole MS; ESI quadrupole orthogonal TOF (Q-TOF); ESI Fourier transform MS systems; desorption/ionization on silicon (DIOS); secondary ion mass spectrometry (SIMS); atmospheric pressure chemical ionization mass spectrometry (APCI-MS); APCI-MS/MS; APCI-(MS)$^n$; atmospheric pressure photoionization mass spectrometry (APPI-MS); APPI-MS/MS; and APPI-(MS)$^n$. Peptide ion fragmentation in tandem MS (MS/MS) arrangements may be achieved using manners established in the art, such as, e.g., collision induced dissociation (CID).

In an embodiment, detection and quantification of biomarkers by mass spectrometry may involve multiple reaction monitoring (MRM), such as described among others by Kuhn et al. 2004 (Proteomics 4: 1175-86).

In an embodiment, MS peptide analysis methods may be advantageously combined with upstream peptide or protein separation or fractionation methods, such as for example with the chromatographic and other methods described herein below.

Chromatography can also be used for measuring biomarkers. As used herein, the term "chromatography" encompasses methods for separating chemical substances, referred to as such and vastly available in the art. In a preferred approach, chromatography refers to a process in which a mixture of chemical substances (analytes) carried by a moving stream of liquid or gas ("mobile phase") is separated into components as a result of differential distribution of the analytes, as they flow around or over a stationary liquid or solid phase ("stationary phase"), between said mobile phase and said stationary phase. The stationary phase may be usually a finely divided solid, a sheet of filter material, or a thin film of a liquid on the surface of a solid, or the like. Chromatography is also widely applicable for the separation of chemical compounds of biological origin, such as, e.g., amino acids, proteins, fragments of proteins or peptides, etc.

Chromatography as used herein may be preferably columnar (i.e., wherein the stationary phase is deposited or packed in a column), preferably liquid chromatography, and yet more preferably HPLC. While particulars of chromatography are well known in the art, for further guidance see, e.g., Meyer M., 1998, ISBN: 047198373X, and "Practical HPLC Methodology and Applications", Bidlingmeyer, B. A., John Wiley & Sons Inc., 1993.

Exemplary types of chromatography include, without limitation, high-performance liquid chromatography (HPLC), normal phase HPLC (NP-HPLC), reversed phase HPLC (RP-HPLC), ion exchange chromatography (IEC), such as cation or anion exchange chromatography, hydrophilic interaction chromatography (HILIC), hydrophobic interaction chromatography (HIC), size exclusion chromatography (SEC) including gel filtration chromatography or gel permeation chromatography, chromatofocusing, affinity chromatography such as immuno-affinity, immobilised metal affinity chromatography, and the like.

In an embodiment, chromatography, including single-, two- or more-dimensional chromatography, may be used as a peptide fractionation method in conjunction with a further peptide analysis method, such as for example, with a downstream mass spectrometry analysis as described elsewhere in this specification.

Further peptide or polypeptide separation, identification or quantification methods may be used, optionally in conjunction with any of the above described analysis methods, for measuring biomarkers in the present disclosure. Such methods include, without limitation, chemical extraction partitioning, isoelectric focusing (IEF) including capillary isoelectric focusing (CIEF), capillary isotachophoresis (CITP), capillary electrochromatography (CEC), and the like, one-dimensional polyacrylamide gel electrophoresis (PAGE), two-dimensional polyacrylamide gel electrophoresis (2D-PAGE), capillary gel electrophoresis (CGE), capillary zone electrophoresis (CZE), micellar electrokinetic chromatography (MEKC), free flow electrophoresis (FFE), etc.

The various aspects and embodiments taught herein may further rely on comparing the quantity of MCAM measured in samples with reference values of the quantity of MCAM, wherein said reference values represent known predictions, diagnoses and/or prognoses of the conditions, symptoms and/or parameters as described herein.

For example, distinct reference values may represent the prediction of a risk (e.g., an abnormally elevated risk) of having a condition, symptom and/or parameter value according to the invention vs. the prediction of no or normal risk of having such. In another example, distinct reference values may represent predictions of differing degrees of risk of having a condition, symptom and/or parameter value according to the invention.

In a further example, distinct reference values can represent the diagnosis of a condition, symptom and/or parameter value according to the invention vs. the diagnosis of the absence thereof (such as, e.g., the diagnosis of healthy, or recovered from a condition, symptom and/or parameter value according to the invention, etc.). In another example, distinct reference values may represent the diagnosis of a condition, symptom and/or a representative parameter thereof according to the invention of varying severity.

In yet another example, distinct reference values may represent a good prognosis for a condition, symptom and/or parameter value according to the invention vs. a poor prognosis thereof. In a further example, distinct reference values may represent varyingly favourable or unfavourable prognoses for a condition or symptom, as determined by the parameters according to the invention.

Such comparison may generally include any means to determine the presence or absence of at least one difference and optionally of the size of such different between values or profiles being compared. A comparison may include a visual inspection, an arithmetical or statistical comparison of measurements. Such statistical comparisons include, but are not limited to, applying a rule. If the values or biomarker profiles comprise at least one standard, the comparison to determine a difference in said values or biomarker profiles may also include measurements of these standards, such that measurements of the biomarker are correlated to measurements of the internal standards.

Reference values for the quantity of MCAM may be established according to known procedures previously employed for other biomarkers.

For example, a reference value of the quantity of MCAM for a particular prediction, diagnosis and/or prognosis of a condition, symptom and/or parameter value according to the invention may be established by determining the quantity of MCAM in sample(s) from one individual or from a population of individuals characterised by said particular prediction, diagnosis and/or prognosis of a condition, symptom and/or parameter value according to the invention (i.e., for whom said prediction, diagnosis and/or prognosis of the specific condition, symptom and/or parameter value according to the invention holds true). Such population may comprise without limitation ≥2, ≥10, ≥100, or even several hundreds or more individuals.

Hence, by means of an illustrative example, reference values of the quantity of MCAM for the diagnoses of a condition, symptom and/or parameter value according to the invention vs. the absence thereof may be established by determining the quantity of MCAM in sample(s) from one individual or from a population of individuals diagnosed (e.g., based on other adequately conclusive means, such as, for example, clinical signs and symptoms, imaging, ECG, etc.) as, respectively, having or not having the specific condition, symptom and/or parameter value according to the invention.

In an embodiment, reference value(s) as intended herein may convey absolute quantities of MCAM. In another embodiment, the quantity of MCAM in a sample from a tested subject may be determined directly relative to the reference value (e.g., in terms of increase or decrease, or fold-increase or fold-decrease). Advantageously, this may allow to compare the quantity of MCAM in the sample from the subject with the reference value (in other words to measure the relative quantity of MCAM in the sample from the subject vis-à-vis the reference value) without the need to first determine the respective absolute quantities of MCAM.

The expression level or presence of a biomarker in a sample of a patient may sometimes fluctuate, i.e. increase or decrease significantly without change (appearance of, worsening or improving of) symptoms. In such an event, the marker change precedes the change in symptoms and becomes a more sensitive measure than symptom change. Therapeutic intervention can be initiated earlier and be more effective than waiting for deteriorating symptoms. Symptoms can be (but not limited to): shortness of breath, oedema in lower extremities, heart palpitations, fatigue, etc. Early intervention at a more benign status may be carried out safely at home, which is a major improvement from treating seriously deteriorated patients in the emergency room.

Measuring the MCAM level of the same patient at different time points can in such a case thus enable the continuous monitoring of the status of the patient and can lead to prediction of worsening or improvement of the patient's condition. A home or clinical test kit or device as indicated herein can be used for this continuous monitoring. One or more reference values or ranges of MCAM levels linked to a certain disease state for such a test can e.g. be determined beforehand or during the monitoring process over a certain period of time in said subject. Alternatively, these reference values or ranges can be established through data sets of several patients with highly similar disease phenotypes. A sudden deviation of the MCAM levels from said reference value or range can predict the worsening of the condition of the patient (e.g. at home or in the clinic) before the (often severe) symptoms actually can be felt or observed.

The invention therefore also provides a method or algorithm for determining a significant change in the level of the MCAM marker in a certain patient, which is indicative for change (worsening or improving) in clinical status. In addition, the invention allows establishing the diagnosis that the subject is recovering or has recovered from the condition.

In an embodiment the present methods may include a step of establishing such reference value(s). In an embodiment, the present kits and devices may include means for establishing a reference value of the quantity of MCAM for a particular prediction, diagnosis and/or prognosis of a condition, symptom and/or parameter value according to the invention. Such means may for example comprise one or more samples (e.g., separate or pooled samples) from one or more individuals characterised by said particular prediction, diagnosis and/or prognosis of this condition, symptom and/or parameter value according to the invention.

The various aspects and embodiments taught herein may further entail finding a deviation or no deviation between the quantity of MCAM measured in a sample from a subject and a given reference value.

A "deviation" of a first value from a second value may generally encompass any direction (e.g., increase: first value >second value; or decrease: first value <second value) and any extent of alteration.

For example, a deviation may encompass a decrease in a first value by, without limitation, at least about 10% (about 0.9-fold or less), or by at least about 20% (about 0.8-fold or less), or by at least about 30% (about 0.7-fold or less), or by at least about 40% (about 0.6-fold or less), or by at least about 50% (about 0.5-fold or less), or by at least about 60% (about 0.4-fold or less), or by at least about 70% (about 0.3-fold or less), or by at least about 80% (about 0.2-fold or less), or by at least about 90% (about 0.1-fold or less), relative to a second value with which a comparison is being made.

For example, a deviation may encompass an increase of a first value by, without limitation, at least about 10% (about 1.1-fold or more), or by at least about 20% (about 1.2-fold or more), or by at least about 30% (about 1.3-fold or more), or by at least about 40% (about 1.4-fold or more), or by at least about 50% (about 1.5-fold or more), or by at least about 60% (about 1.6-fold or more), or by at least about 70% (about 1.7-fold or more), or by at least about 80% (about 1.8-fold or more), or by at least about 90% (about 1.9-fold or more), or by at least about 100% (about 2-fold or more), or by at least about 150% (about 2.5-fold or more), or by at least about 200% (about 3-fold or more), or by at least about 500% (about 6-fold or more), or by at least about 700% (about 8-fold or more), or like, relative to a second value with which a comparison is being made.

Preferably, a deviation may refer to a statistically significant observed alteration. For example, a deviation may refer to an observed alteration which falls outside of error margins of reference values in a given population (as expressed, for example, by standard deviation or standard error, or by a predetermined multiple thereof, e.g., ±1×SD or ±2×SD, or ±1×SE or ±2×SE). Deviation may also refer to a value falling outside of a reference range defined by values in a given population (for example, outside of a range which comprises ≥40%, ≥50%, ≥60%, ≥70%, ≥75% or ≥80% or ≥85% or ≥90% or ≥95% or even ≥100% of values in said population).

In a further embodiment, a deviation may be concluded if an observed alteration is beyond a given threshold or cut-off. Such threshold or cut-off may be selected as generally known in the art to provide for a chosen sensitivity and/or specificity of the prediction, diagnosis and/or prognosis methods, e.g., sensitivity and/or specificity of at least 50%, or at least 60%, or at least 70%, or at least 80%, or at least 85%, or at least 90%, or at least 95%.

For example, in an embodiment, an elevated quantity of MCAM in the sample from the subject—preferably at least about 1.1-fold elevated, or at least about 1.2-fold elevated, more preferably at least about 1.3-fold elevated, even more preferably at least about 1.4-fold elevated, yet more preferably at least about 1.5-fold elevated, such as between about 1.1-fold and 3-fold elevated or between about 1.5-fold and 2-fold elevated—compared to a reference value representing the prediction or diagnosis of absence of or representing a good prognosis for a condition, symptom and/or parameter value according to the invention indicates that the subject has or is at risk of having that condition, symptom and/or parameter value according to the invention or indicates a poor prognosis for that condition, symptom and/or parameter value according to the invention in the subject.

When a deviation is found between the quantity of MCAM in a sample from a subject and a reference value representing a certain prediction, diagnosis and/or prognosis, said deviation is indicative of or may be attributed to the conclusion that the prediction, diagnosis and/or prognosis of a condition, symptom and/or parameter value according to the invention in said subject is different from that represented by the reference value.

When no deviation is found between the quantity of MCAM in a sample from a subject and a reference value representing a certain prediction, diagnosis and/or prognosis, the absence of such deviation is indicative of or may be attributed to the conclusion that the prediction, diagnosis and/or prognosis of a condition, symptom and/or parameter value according to the invention in said subject is substantially the same as that represented by the reference value.

The above considerations apply analogously to biomarker profiles.

When two or more different biomarkers are determined in a subject, their respective presence, absence and/or quantity may be together represented as a biomarker profile, the values for each measured biomarker making a part of said profile. As used herein, the term "profile" includes any set of data that represents the distinctive features or characteristics associated with a condition of interest, such as with a particular prediction, diagnosis and/or prognosis of a condition, symptom and/or parameter value according to the invention. The term generally encompasses inter alia nucleic acid profiles, such as for example genotypic profiles (sets of genotypic data that represents the genotype of one or more genes associated with a condition of interest), gene copy number profiles (sets of gene copy number data that represents the amplification or deletion of one or more genes associated with a condition of interest), gene expression profiles (sets of gene expression data that represents the mRNA levels of one or more genes associated with a condition of interest), DNA methylation profiles (sets of methylation data that represents the DNA methylation levels of one or more genes associated with a condition of interest), as well as protein, polypeptide or peptide profiles, such as for example protein expression profiles (sets of protein expression data that represents the levels of one or more proteins associated with a condition of interest), protein activation profiles (sets of data that represents the activation or inactivation of one or more proteins associated with a condition of interest), protein modification profiles (sets of data that represents the modification of one or more proteins associated with a condition of interest), protein cleavage profiles (sets of data that represent the proteolytic cleavage of one or more proteins associated with a condition of interest), as well as any combinations thereof.

Biomarker profiles may be created in a number of ways and may be the combination of measurable biomarkers or aspects of biomarkers using methods such as ratios, or other more complex association methods or algorithms (e.g., rule-based methods). A biomarker profile comprises at least two measurements, where the measurements can correspond to the same or different biomarkers. A biomarker profile may also comprise at least three, four, five, 10, 20, 30 or more measurements. In one embodiment, a biomarker profile comprises hundreds, or even thousands, of measurements.

Hence, for example, distinct reference profiles may represent the prediction of a risk (e.g., an abnormally elevated risk) of having a condition, symptom and/or parameter value according to the invention vs. the prediction of no or normal risk of having such. In another example, distinct reference profiles may represent predictions of differing degrees of risk of having a condition, symptom and/or parameter value according to the invention.

In a further example, distinct reference profiles can represent the diagnosis of a condition, symptom and/or parameter value according to the invention vs. the diagnosis no such condition, symptom and/or parameter value (such as, e.g., the diagnosis of healthy, recovered from that condition or symptom according to the invention, etc.). In another example, distinct reference profiles may represent the diagnosis of a condition or symptom according to the invention of varying severity.

In a yet another example, distinct reference profiles may represent a good prognosis for a condition, symptom and/or parameter value according to the invention vs. a poor prognosis thereof. In a further example, distinct reference profiles may represent varyingly favourable or unfavourable prognoses for a condition, symptom and/or parameter value according to the invention.

Reference profiles used herein may be established according to known procedures previously employed for other biomarkers.

For example, a reference profile of the quantity of MCAM and the presence or absence and/or quantity of one or more other biomarkers related to the conditions, symptoms or parameters according to the invention for a particular prediction, diagnosis and/or prognosis may be established by determining the profile in sample(s) from one individual or from a population of individuals characterised by said particular prediction, diagnosis and/or prognosis (i.e., for whom said prediction, diagnosis and/or prognosis holds true). Such population may comprise without limitation ≥2, ≥10, ≥100, or even several hundreds or more individuals.

Hence, by means of an illustrative example, reference profiles for the diagnoses of AHF vs. no AHF may be established by determining the biomarker profiles in sample(s) from one individual or from a population of individuals diagnosed as, respectively, having or not having AHF.

In an embodiment the present methods may include a step of establishing such reference profile(s). In an embodiment, the present kits and devices may include means for establishing a reference profile for a particular prediction, diagnosis and/or prognosis. Such means may for example comprise one or more samples (e.g., separate or pooled samples) from one or more individuals characterised by said particular prediction, diagnosis and/or prognosis.

Further, art-known multi-parameter analyses may be employed mutatis mutandis to determine deviations between groups of values and profiles generated there from (e.g., between sample and reference biomarker profiles).

When a deviation is found between the sample profile and a reference profile representing a certain prediction, diagnosis and/or prognosis, said deviation is indicative of or may be attributed to the conclusion that the prediction, diagnosis and/or prognosis in said subject is different from that represented by the reference profile.

When no deviation is found between the sample profile and a reference profile representing a certain prediction, diagnosis and/or prognosis, the absence of such deviation is indicative of or may be attributed to the conclusion that the prediction, diagnosis and/or prognosis in said subject is substantially the same as that represented by the reference profile.

The present invention further provides kits or devices for diagnosis of the conditions, symptoms and/or parameters according to the invention, comprising means for detecting the level of the MCAM marker in a sample of the patient. In a more preferred embodiment, such a kit or kits of the invention can be used in clinical settings or at home. The kit according to the invention can be used for diagnosing, for monitoring the effectiveness of treatment of a subject suffering from a condition or symptom according to the invention with an agent, or for preventive screening of subjects for the occurrence of a condition, symptom and/or specific parameter value according to the invention in said subject.

In a clinical setting, the kit or device can be in the form of a bed-side device or in an emergency team setting, e.g. as part of the equipment of an ambulance or other moving emergency vehicle or team equipment or as part of a first-aid kit. The diagnostic kit or device can assist a medical practitioner, a first aid helper, or nurse to decide whether the patient under observation is developing an acute heart failure, after which appropriate action or treatment can be performed.

A home-test kit gives the patient a readout which he can communicate to a medicinal practitioner, a first aid helper or to the emergency department of a hospital, after which appropriate action can be taken. Such a home-test device is of particular interest for people having either a history of, or are at risk of suffering from a condition or symptom, represented by a parameter according to the invention, such as heart failure (e.g. chronic heart failure patients) or have a history or are at risk of suffering from dyspnea (shortness of breath), which may be caused by e.g. acute heart failure, infections, lung-problems, sepsis, etc. Such subjects with a high risk for heart failure or having a history of dyspnea could certainly benefit from having a home test device or kit according to the invention at home, because they can then easily distinguish between an acute heart failure event and another event causing the dyspnea, resulting in an easier way of determining the actions to be taken to resolve the problem.

Typical kits or devices according to the invention comprise the following elements:
a) a means for obtaining a sample from the subject
b) a means or device for measuring the amount of the MCAM marker in said sample and visualizing whether the amount of the MCAM marker in said sample is below or above a certain threshold level or value, indicating whether the subject is suffering from a condition or symptom according to the invention, represented by a parameter as described herein or not.

In any of the embodiments of the invention, the kits or devices can additionally comprise c) means for communicating directly with a medical practitioner, an emergency department of the hospital or a first aid post, indicating that a person is suffering from acute heart failure or not.

The term "threshold level or value" or "reference value" is used interchangeably as a synonym and is as defined herein. It can also be a range of base-line (e.g. "dry weight") values determined in an individual patient or in a group of patients with highly similar disease conditions.

In any of the embodiments of the invention, the device or kit or kits of the invention can additionally comprise means for detecting the level of an additional marker as taught herein.

Any of kits as defined herein can be used as a bed-side device for use by the subject himself or by a clinical practitioner.

In said kit of the invention, the means for obtaining a sample from the subject (a) can be any means for obtaining a sample from the subject known in the art. Examples for obtaining e.g. a blood sample are known in the art and could be any kind of finger or skin prick or lancet based device, which basically pierces the skin and results in a drop of blood being released from the skin. When a urine sample is used, the means for obtaining a sample from the subject can be in the form of an absorbent strip such as the ones used in home pregnancy tests known in the art. In analogy, a saliva sample could be obtained using a mount swab known in the art. Example of blood sampling devices or other sampling devices are for example given in U.S. Pat. Nos. 4,802,493, 4,966,159, 5,099,857, 6,095,988, 5,944,671, 4,553,541, 3,760,809, 5,395,388, 5,212,879, 5,630,828, 5,133,730, 4,653,513, 5,368,047, 5,569,287, 4,360,016, 5,413,006 and U.S. Pat. Applic. 2002/111565, 2004/0096959, 2005/143713, 2005/137525, 2003/0153900, 2003/0088191, WO9955232, WO2005/049107, WO2004/060163, WO02/056751, WO02/100254, WO2003/022330, WO2004/066822, WO97/46157, WO2004/039429, or EP0364621, EP0078724, EP1212138, EP0081975, or EP0292928.

In said kit of the invention, the means or device for measuring the amount of the MCAM marker in said sample (b) can be any means or device that can specifically detect the amount of the MCAM protein in the sample. Examples are systems comprising MCAM specific binding molecules attached to a solid phase, e.g. lateral flow strips or dipstick devices and the like well known in the art. One non-limiting example to perform a biochemical assay is to use a test-strip and labelled antibodies which combination does not require any washing of the membrane. The test strip is well known, for example, in the field of pregnancy testing kits where an anti-hCG antibody is present on the support, and is carried complexed with hCG by the flow of urine onto an immobilised second antibody that permits visualisation. Other non-limiting examples of such home test devices, systems or kits can be found for example in the following U.S. Pat. No. 6,107,045, U.S. Pat. Nos. 6,974,706, 5,108,889, 6,027,944, 6,482,156, 6,511,814, 5,824,268, 5,726,010, 6,001,658 or U.S. patent applications: 2008/0090305 or 2003/0109067.

In a preferred embodiment, the invention provides a lateral flow device or dipstick. Such dipstick comprises a test strip allowing migration of a sample by capillary flow from one end of the strip where the sample is applied to the other end of such strip where presence of an analyte in said sample is measured.

In another embodiment, the invention provides a device comprising a reagent strip. Such reagent strip comprises one or more test pads which when wetted with the sample, provide a color change in the presence of an analyte and/or indicate the concentration of the protein in said sample.

In one preferred embodiment of the kit of the invention, the means or device (1) for measuring the amount of protein in a sample (b) is a solid support (7) having a proximal (2) and distal (3) end, comprising:
 a sample application zone (4) in the vicinity of the proximal end,
 a reaction zone (5) distal to the sample application zone (4), and
 a detection zone (6) distal to the reaction zone (5),
whereby said support has a capillary property that directs a flow of fluid sample applied in the application zone in a direction from the proximal end to the distal end, optionally, the means or device also comprises a source of fluid, e.g. in a container, dropper pipette or vial, enabling viscous samples to flow easier through the strip.

The reaction zone (5) comprises one or more bands (10) of MCAM binding molecule conjugated to a detection agent (e.g. colloidal gold) which MCAM binding molecule conjugate is disposed on the solid support such that it can migrate with the capillary flow of fluid i.e. it is not immobilised. The detection zone (6) comprises one or more capture bands (11) comprising a population of MCAM binding molecules immobilised on the solid support.

When a sample is applied to the sample application zone (4), it migrates towards the reaction zone (5) by capillary flow. Any MCAM present in the sample reacts with the MCAM labelled binding molecule conjugate, and the complex so formed is carried by capillary flow to the detection zone (6). The detection zone (6), having MCAM binding molecules permanently immobilised thereon, captures and immobilises any complex, resulting in a localised concentration of conjugate that can be visualised.

The two zones (5 and 6) as described herein (one zone with the non-fixed conjugates and one zone with the fixed capture antibodies) generally do not overlap. They may be adjacently arranged with an absence or presence of an intervening gap of solid support devoid of band. A band may be disposed on a solid support by any means, for example, absorbed, adsorbed, coated, covalently attached or dried, depending on whether the reagent is required to be mobilised or not.

In order to obtain a semi-quantitative test strip in which only a signal is formed once the MCAM protein level in the sample is higher than a certain predetermined threshold level or value, the reaction zone (5) comprising the non-fixed conjugated MCAM binding molecules, could also comprise a predetermined amount of fixed MCAM capture antibodies. This enables to capture away a certain amount of MCAM protein present in the sample, corresponding to the threshold level or value as predetermined. The remaining amount of MCAM protein (if any) bound by the conjugated or labelled binding molecules can then be allowed to migrate to the detection zone (6). In this case, the reaction zone (6) will only receive labelled binding molecule-MCAM complexes and subsequently only produce a signal if the level of the MCAM protein in the sample is higher than the predetermined threshold level or value.

Another possibility to determine whether the amount of the MCAM protein in the sample is below or above a certain threshold level or value, is to use a primary capturing antibody capturing all MCAM protein present in the sample, in combination with a labeled secondary antibody, developing a certain signal or color when bound to the solid phase. The intensity of the color or signal can then either be compared to a reference color or signal chart indicating that when the intensity of the signal is above a certain threshold signal, the test is positive (i.e. the condition, symptom and/or parameter according to the invention is diagnosed). Alternatively, the amount or intensity of the color or signal can be measured with an electronic device comprising e.g. a light absorbance sensor or light emission meter, resulting in a numerical value of signal intensity or color absorbance formed, which can then be displayed to the subject in the form of a negative result if said numerical value is below the threshold value or a positive result if said numerical value is above the threshold value.

This embodiment is of particular relevance in monitoring the MCAM level in a patient over a period of time.

The reference value or range can e.g. be determined using the home device in a period wherein the subject is free of the conditions or symptoms according to the invention, or wherein the parameters according to the invention are normalized, giving the patient an indication of his base-line MCAM level. Regularly using the home test device will thus enable the subject to notice a sudden change in MCAM levels as compared to the base-line level, which can enable him to contact a medical practitioner.

Alternatively, the reference value can be determined in the subject suffering from the conditions or symptoms according to the invention, or wherein the parameters according to the invention are abnormal, i.e. elevated or decreased, which then indicates his personal MCAM "risk level", i.e. the level of MCAM which indicates he is or will soon be exposed to a condition or symptom according to the invention event. This risk level is interesting for monitoring the disease progression or for evaluating the effect of the treatment. Reduction of the MCAM level as compared to the risk level indicates that the condition of the patient is improving.

Furthermore, the reference value or level can be established through combined measurement results in subjects with highly similar disease states or phenotypes.

Non-limiting examples of such semi-quantitative tests known in the art, the principle of which could be used for the home test device according to the present invention are the HIV/AIDS test or Prostate Cancer tests sold by Sanitoets. The home prostate test is a rapid test intended as an initial semi-quantitative test to detect PSA blood levels higher than 4 ng/ml in whole blood. The typical home self-test kit comprises the following components: a test device to which the blood sample is to be administered and which results in a signal when the protein level is above a certain threshold level, an amount of diluent e.g. in dropper pipette to help the transfer of the analytes (i.e. the protein of interest) from the sample application zone to the signal detection zone, optionally an empty pipette for blood specimen collection, a finger pricking device, optionally a sterile swab to clean the area of pricking and instructions of use of the kit.

Similar tests are also known for e.g. breast cancer detection and CRP-protein level detection in view of cardiac risk home tests. The latter test encompasses the sending of the test result to a laboratory, where the result is interpreted by a technical or medical expert. Such telephone or internet based diagnosis of the patient's condition is of course possible and advisable with most of the kits, since interpretation of the test result is often more important than conducting the test. When using an electronic device as mentioned above which gives a numerical value of the level of protein present in the sample, this value can of course easily be communicated through telephone, mobile telephone, satellite phone, E-mail, internet or other communication means, warning a hospital, a medicinal practitioner or a first aid team that a person is suffering from an acute heart failure. A non-limiting example of such a system is disclosed in U.S. Pat. No. 6,482,156.

Reference is made in the description below to the drawings which exemplify particular embodiments of the invention; they are not at all intended to be limiting. The skilled person may adapt the device and substituent components and features according to the common practices of the person skilled in the art.

Figure 5:
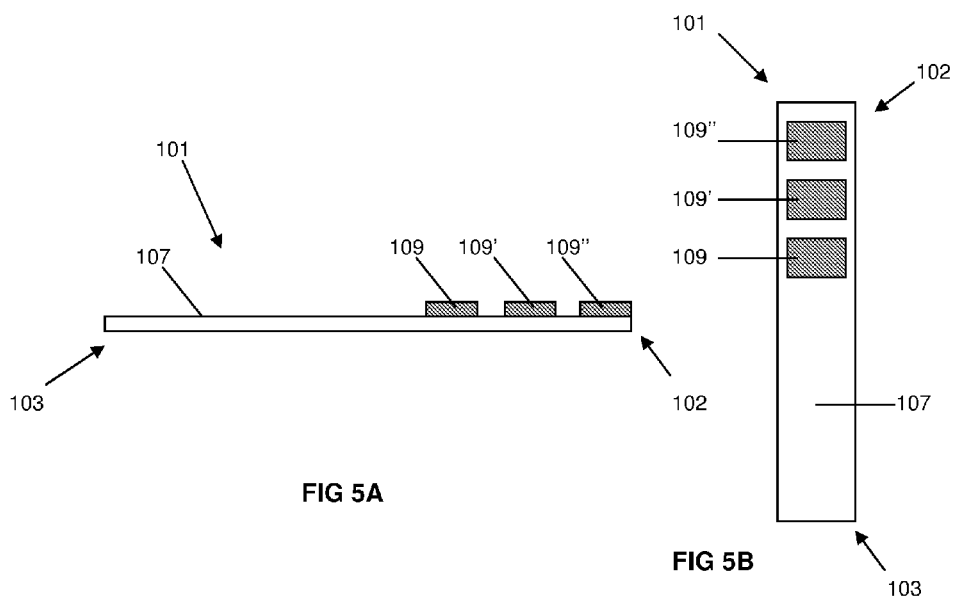
FIG. 5 A-B shows a side view and a top view, respectively, of a reagent strip according to the invention comprising several test pads.

FIGS. 3A and B shows a preferred embodiment of a test strip of the invention. The strip (1) includes a proximal end (2) and a distal end (3). A sample application zone (4) is provided in the proximal end (2), a reaction zone (5) is adjacent thereto and a detection zone (6) is in the vicinity of the distal end (3). A sample may be deposited onto the solid support (7) at the application zone (4) to transfer by capillary action to the detection zone (6). A protective layer (8) that covers either or both the surfaces of the solid support (7), except for a region of the sample application zone (4) may be provided. Such protective layer protects the sample and chemical constituency of the strip from contamination and evaporation. One or more absorbent pads (9) in capillary contact with the sample application zone (4) of the solid support (7) may absorb and release sample as necessary; such pad (9) is typically placed on the surface of the solid support (7) that is the same or opposing the sample application zone (4). In FIG. 5B, the absorbent pad (9) is part of the sample application zone (4). One or more other absorbent pads (9') in capillary may be placed in contact with the detection zone (6) of the solid support (7), distal to any capture bands (11), (14). These pads (9') may absorb fluid that has passed through the solid support; such pad (9') is typically placed on the surface of the solid support (7) that is the same or opposing the sample application zone (4). The solid support (7) may made from any suitable material that has a capillary action property, and may have the same properties as described above. It should also be capable of supporting a substance (e.g. non-immobilised MCAM binding molecule), which, when hydrated, can migrate across the solid support by a capillary action fluid flow.

The solid support (7) may also comprise a band of MCAM binding molecule conjugate (10), located in the reaction zone (5), at a position distal to the sample application zone (4). Any MCAM in the sample is carried by capillary action towards this band (10), where it reacts with the permanently immobilised MCAM binding molecule conjugate.

The MCAM binding molecule conjugate may be associated with or attached to a detection agent to facilitate detection. Examples of lab detection agents include, but are not limited to, luminescent labels; colorimetric labels, such as dyes; fluorescent labels; or chemical labels, such as electroactive agents (e.g., ferrocyanide); enzymes; radioactive labels; or radiofrequency labels. More commonly, the detection agent is a particle. Examples of particles useful in the practice of the invention include, but are not limited to, colloidal gold particles; colloidal sulphur particles; colloidal selenium particles; colloidal barium sulfate particles; colloidal iron sulfate particles; metal iodate particles; silver halide particles; silica particles; colloidal metal (hydrous) oxide particles; colloidal metal sulfide particles; colloidal lead selenide particles; colloidal cadmium selenide particles; colloidal metal phosphate particles; colloidal metal ferrite particles; any of the above-mentioned colloidal particles coated with organic or inorganic layers; protein or peptide molecules; liposomes; or organic polymer latex particles, such as polystyrene latex beads. Preferable particles are colloidal gold particles. Colloidal gold may be made by any conventional means, such as the methods outlined in G. Frens, 1973 Nature Physical Science, 241:20 (1973). Alternative methods may be described in U.S. Pat. Nos. 5,578,577, 5,141,850; 4,775,636; 4,853,335; 4,859,612; 5,079,172; 5,202,267; 5,514,602; 5,616,467; 5,681,775.

The solid support (7) further comprises one or more capture bands (11) in the detection zone (6). A capture band comprises a population of MCAM binding molecule permanently immobilised thereon. The MCAM: MCAM-binding molecule conjugate complex formed in the reaction zone (5) migrates towards the detection zone (6) where said band (11) captures migrating complex, and concentrates it, allowing it to be visualised either by eye, or using a machine reader. The MCAM binding molecule present in the reaction zone (5) and in the detection zone (6) may reaction to the same part of MCAM or may react to different parts of MCAM.

One or more controls bands (12) may be present on the solid support (7). For example, a non-immobilised peptide (12) might be present in the sample application zone (4), which peptide does not cross-react with any of bands of MCAM binding molecule (13) or (14). As the sample is applied, it migrates towards the reaction zone (5), where an anti-peptide antibody conjugate is disposed (13), and where a complex peptide-antibody complex is formed. Said complex migrates towards the detection zone (6), where a capture band (14) of anti-peptide antibody is immobilised on the solid support, and which concentrates said complex enabling visualisation. The control capture band (14) is located separately from the MCAM capture band (11), therefore, a positive reaction can be seen distinct from the detection reaction if the assay is working correctly.

A particular advantage of a control according to the invention is that they are internal controls—that is, the control against which the MCAM measurement results may be compared is present on the individual solid support. Therefore, the controls according to the invention may be used to correct for variability in the solid support, for example. Such correction would be impractical with external controls that are based, for example, on a statistical sampling of supports. Additionally, lot-to-lot, and run-to-run, variations between different supports may be minimized by use of control binding agents and control agents according to the invention. Furthermore, the effects of non-specific binding may be reduced. All of these corrections would be difficult to accomplish using external, off-support, controls.

During the assay, MCAM from the sample and the MCAM binding molecule conjugate combine and concentrate on the solid support (7). This combination results in a concentration of compounds that may can be visualised above the background colour of the solid support (7). The compounds may be formed from a combination of above-mentioned compounds, including antibodies, detection agents, and other particles associated with the reaction and detection zones. Based on the particular assay being performed, the reaction and detection zones may be selectively implemented to achieve an appropriate dynamic range which may be linear or non-linear.

Figure 6:
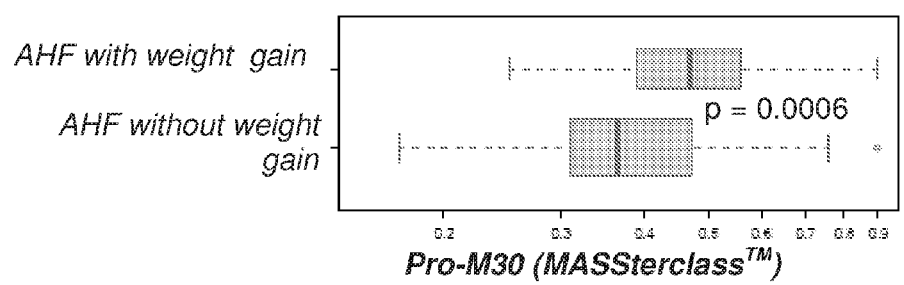
FIG. 6: illustrates in box and whisker plots the correlation between weight gain and MCAM levels in AHF patients at admission.

A solid support (7) for performing the assay may be housed within the cartridge (20) as shown, for example, in FIG. 6. The cartridge is preferably watertight against urine, except for one or more openings. The solid support (7) may be exposed through an opening (21) in the cartridge to provide an application zone (4) in proximal end (2), and another opening (22) to enable reading of detection zone (6) close to the distal end (3). Cartridge (20) may include a sensor code (23) for communicating with a reading device.

The presence and/or concentration of MCAM in a sample can be measured by surface plasmon resonance (SPR) using a chip having MCAM binding molecule immobilized thereon, fluorescence resonance energy transfer (FRET), bioluminescence resonance energy transfer (BRET), fluorescence quenching, fluorescence polarization measurement or other means known in the art. Any of the binding assays described can be used to determine the presence and/or concentration of MCAM in a sample. To do so, MCAM binding molecule is reacted with a sample, and the concentration of MCAM is measured as appropriate for the binding assay being used. To validate and calibrate an assay, control reactions using different concentrations of standard MCAM and/ or MCAM binding molecule can be performed. Where solid phase assays are employed, after incubation, a washing step is performed to remove unbound MCAM. Bound, MCAM is measured as appropriate for the given label (e.g., scintillation counting, fluorescence, antibody-dye etc.). If a qualitative result is desired, controls and different concentrations may not be necessary. Of course, the roles of MCAM and MCAM binding molecule may be switched; the skilled person may adapt the method so MCAM binding molecule is applied to sample, at various concentrations of sample.

A MCAM binding molecule according to the invention is any substance that binds specifically to MCAM. Examples of a MCAM binding molecule useful according to the present invention, includes, but is not limited to an antibody, a polypeptide, a peptide, a lipid, a carbohydrate, a nucleic acid, peptide-nucleic acid, small molecule, small organic molecule, or other drug candidate. A MCAM binding molecule can be natural or synthetic compound, including, for example, synthetic small molecule, compound contained in extracts of animal, plant, bacterial or fungal cells, as well as conditioned medium from such cells. Alternatively, MCAM binding molecule can be an engineered protein having binding sites for MCAM. According to an aspect of the invention, a MCAM binding molecule binds specifically to MCAM with an affinity better than $10^{-6}$ M. A suitable MCAM binding molecule e can be determined from its binding with a standard sample of MCAM. Methods for determining the binding between MCAM binding molecule and MCAM are known in the art. As used herein, the term antibody includes, but is not limited to, polyclonal antibodies, monoclonal antibodies, humanised or chimeric antibodies, engineered antibodies, and biologically functional antibody fragments (e.g. scFv, nanobodies, Fv, etc) sufficient for binding of the antibody fragment to the protein. Such antibody may be commercially available antibody against MCAM, such as, for example, a mouse, rat, human or humanised monoclonal antibody.

In a preferred embodiment, the binding molecule or agent is capable of binding both the mature membrane- or cell-bound MCAM protein or fragment. In a more preferred embodiment, the binding agent or molecule is specifically binding or detecting the soluble form, preferably the plasma circulating form of MCAM, as defined herein.

According to one aspect of the invention, the MCAM binding molecule is labelled with a tag that permits detection with another agent (e.g. with a probe binding partner). Such tags can be, for example, biotin, streptavidin, his-tag, myc tag, maltose, maltose binding protein or any other kind of tag known in the art that has a binding partner. Example of associations which can be utilised in the probe:binding partner arrangement may be any, and includes, for example biotin: streptavidin, his-tag:metal ion (e.g. $Ni^{2+}$), maltose:maltose binding protein.

In another embodiment, the invention provides a simple and accurate colorimetric reagent strip and method for measuring presence of MCAM in a sample. More in particular, the present invention also relates to a device comprising a reagent strip. The present reagent strip comprises a solid support which is provided with at least one test pad for measuring the presence of MCAM in a sample. Said test pad preferably comprises a carrier matrix incorporating a reagent composition capable of interacting with MCAM to produce a measurable response, preferably a visually or instrumentally measurable response. The reagent strip may be manufactured in any size and shape, but in general the reagent strip is longer than wide. The solid support may be composed of any suitable material and is preferably made of firm or stiff material such as cellulose acetate, polyethylene terephthalate, polypropylene, polycarbonate or polystyrene. In general, the carrier matrix is an absorbent material that allows the urine sample to move, in response to capillary forces, through the carrier matrix to contact the reagent composition and produce a detectable or measurable color transition. The carrier matrix can be any substance capable of incorporating the chemical reagents required to perform the assay of interest, as long as the carrier matrix is substantially inert with respect to the chemical reagents, and is porous or absorbent relative to the soluble components of the liquid test sample. The expression "carrier matrix" refers to either bibulous or nonbibulous matrices that are insoluble in water and other physiological fluids and maintain their structural integrity when exposed to water and other physiological fluids. Suitable bibulous matrices include filter paper, sponge materials, cellulose, wood, woven and nonwoven fabrics and the like. Nonbibulous matrices include glass fiber, polymeric films, and preformed or microporous membranes. Other suitable carrier matrices include hydrophilic inorganic powders, such as silica gel, alumina, diatomaceous earth and the like; argillaceous substances; cloth; hydrophilic natural polymeric materials, particularly cellulose material, like cellulosic beads, and especially fibercontaining papers such as filter paper or chromatographic paper; synthetic or modified naturally-occurring polymers, such as crosslinked gelatin, cellulose acetate, polyvinyl chloride, polyacrylamide, cellulose, polyvinyl alcohol, polysulfones, polyesters, polyacrylates, polyurethanes, crosslinked dextran, agarose, and other such crosslinked and noncrosslinked water-insoluble hydrophilic polymers. Hydrophobic and nonabsorptive substances are not suitable for use as the carrier matrix of the present invention. The carrier matrix can be of different chemical compositions or a mixture of chemical compositions. The matrix also can vary in regards to smoothness and roughness combined with hardness and softness. However, in every instance, the carrier matrix comprises a hydrophilic or absorptive material. The carrier matrix is most advantageously constructed from bibulous filter paper or nonbibulous polymeric films. A preferred carrier matrix is a hydrophilic, bibulous matrix, including cellulosic materials, such as paper, and preferably filter paper or a nonbibulous matrix, including polymeric films, such as a polyurethane or a crosslinked gelatin. A reagent composition which produces a colorimetric change when reacted with MCAM in a sample can be homogeneously incorporated into the carrier matrix, and the carrier matrix then holds the reagent composition homogeneously throughout the carrier matrix while maintaining carrier matrix penetrability by the predetermined component of the test sample. Examples of suitable reagent compositions may include for instance a MCAM binding molecule in case of an antibody-based technique, or pH buffer in case of enzymatic detection. The reagent composition is preferably dried and stabilized onto a test pad adhered to at least one end of a solid support. The test pad onto which the reagent composition is absorbed and dried, is preferably made of a membrane material that shows minimal background color. Preferably, the test pad may be constructed of acid or base washed materials in order to minimize background color. In another embodiment the reagent composition which is dried onto the reagent strip further comprises wetting agents to reduce brittleness of the test pad. Non-limiting examples of preferred wetting agents include TritonX-100, Bioterg, glycerol, 0 Tween, and the like. The reagent composition can be applied to the reagent strip by any method known in the art. For example, the carrier matrix from which the test pads are made may be dipped into a solution of the reagent composition and dried according to techniques known in the art. A reagent strip according to the invention may be provided with multiple test pads to assay for more than one analyte in a urine sample. A reagent strip may be provided comprising a solid support provided with one or more test pads including test pads for measuring the presence of one or more analytes selected from the group comprising proteins such as (acute) heart failure markers, systolic dysfunction markers BNP, NT-pro-BNP or fragments thereof, kidney dysfunction markers Cystatin C, NGAL, U-Albumin, γ-GT, NAG, A1M, B1M, creatinine, vasopression, aldosteron, angiotensin, ACE or fragments thereof, blood, leukocytes, ureum, nitrite, glucose, ketones, bilirubin, urobilinogen, proteins in general and/or a pH test pad, and/or a test pad for measuring specific gravity. in the alternative or in addition hereof, analytes representative of fluid homeostatic imbalance, fluid build-up or fluid decrease, increased or decreased vascular filling volume and/or pressure, weight gain or loss, edema or dehydration, systolic dysfunction, (acute) heart failure, LVEF, LVEDP, cardiac filling pressure may be included on the test pad.

A possible embodiment of a reagent strip 101 according to the invention is depicted diagrammatically in FIG. 5A-B. The strip 101 includes a proximal end 102 and a distal end 103. Various test pads 109, 109', 109" on which the reagent compositions are provided at the proximal end 102 on a solid support 107 of the reagent strip. The strip must be designed in such a way that it can be wetted with a sufficiently large amount of sample, optionally diluted by a physiological fluid improving the capillary flow of a viscous sample such as blood or saliva and the like.

A reagent strip as defined herein is used as follows. Briefly, one or more test pad areas of the reagent strip of the invention is dipped into a sample or a small amount of sample is applied to the reagent strip onto the test pad area(s). A color development which can be analyzed visually or by reflectometry occurs on the reagent strip within a short time, usually within 0.5 to 10 minutes. The change in color of the reagent area on the test pad upon reacting with MCAM is preferably directly proportional to the concentration of MCAM in the patient sample. The color intensity that develops on the test pad may be determined visually or by a reflectance-based reader, for example. Color development at the test pad area(s) is compared to a reference color or colors to determine an estimate of the amount of MCAM present in the sample The color intensity that develops on the test pad is compared to at least one, and preferably at least two standard color shades that correspond to a range of MCAM concentration determined by application of a correction factor.

The reagent strip may further comprises a fluorescent or infrared dye, applied either to the support strip or incorporated into a test pad, which ensures proper alignment of the reagent strip in an apparatus having a detection system for the detectable or measurable response.

In another embodiment, the invention also relates to a test pad for measuring the presence of MCAM in a sample. Preferably said test pad comprises a carrier matrix incorporating a reagent composition capable of interacting with MCAM to produce a measurable response, preferably a visually or instrumentally measurable response. In another preferred embodiment the invention provides a test pad according as define herein for use in on a reagent strip, preferably on a reagent strip as defined herein.

The specific-binding agents, peptides, polypeptides, proteins, biomarkers etc. in the present kits may be in various forms, e.g., lyophilised, free in solution or immobilised on a solid phase. They may be, e.g., provided in a multi-well plate or as an array or microarray, or they may be packaged separately and/or individually. The may be suitably labelled as taught herein. Said kits may be particularly suitable for performing the assay methods of the invention, such as, e.g., immunoassays, ELISA assays, mass spectrometry assays, and the like.

The above aspects and embodiments are further supported by the following non-limiting examples.

EXAMPLES

Example 1

MASSterclass Targeted Protein Quantitation for Early Validation of Candidate Markers Derived from Discovery MASSterclass Experimental Setup MASSterclass assays use targeted tandem mass spectrometry with stable isotope dilution as an end-stage peptide quantitation system (also called Multiple Reaction Monitoring (MRM) and Single Reaction Monitoring (SRM)). The targeted peptide is specific (i.e., proteotypic) for the specific protein of interest. i.e., the amount of peptide measured is directly related to the amount of protein in the original sample. To reach the specificity and sensitivity needed for biomarker quantitation in complex samples, peptide fractionations precede the end-stage quantitation step.

A suitable MASSterclass assay may include the following steps:
Plasma/serum sample
Depletion of human albumin and IgG (complexity reduction on protein level) using affinity capture with anti-albumin and anti-IgG antibodies using ProteoPrep spin columns (Sigma Aldrich)
Spiking of known amounts of isotopically labelled peptides. This peptide has the same amino acid sequence as the proteotypic peptide of interest, typically with one isotopically labelled amino acid built in to generate a mass difference. During the entire process, the labelled peptide has identical chemical and chromatographic behaviour as the endogenous peptide, except during the end-stage quantitation step which is based on molecular mass.
Tryptic digest. The proteins in the depleted serum/plasma sample are digested into peptides using trypsin. This enzyme cleaves proteins C-terminally from lysine and arginine, except when a proline is present C-terminally of the lysine or arginine. Before digestion, proteins are denatured by boiling, which renders the protein molecule more accessible for the trypsin activity during the 16 h incubation at 37° C.
First peptide-based fractionation: Free Flow Electrophoresis (FFE; BD Diagnostic) is a gel-free, fluid separation technique in which charged molecules moving in a continuous laminar flow are separated through an electrical field perpendicular to the flow. The electrical field causes the charged molecules to separate in the pH gradient according to their isoelectric point (pI). Only those fractions containing the monitored peptides are selected for further fractionation and LC-MS/MS analysis. Each peptide of interest elutes from the FFE chamber at a specific fraction number, which is determined during protein assay development using the synthetic peptide homologue. Specific fractions or fraction pools (multiplexing) proceed to the next level of fractionation.
Second peptide-based fractionation: Phenyl HPLC (XBridge Phenyl; Waters) separates peptides according to hydrophobicity and aromatic nature of amino acids present in the peptide sequence. Orthogonality with the back-end C18 separation is achieved by operating the column at an increased pH value (pH 10). As demonstrated by Gilar et al. 2005, *J Sep Sci* 28(14): 1694-

1703), pH is by far the most drastic parameter to alter peptide selectivity in RP-HPLC. Each peptide of interest elutes from the Phenyl column at a specific retention time, which is determined during protein assay development using the synthetic peptide homologue. The use of an external control system, in which a mixture of 9 standard peptides is separated upfront a batch of sample separations, allows adjusting the fraction collection in order to correct for retention time shifts. The extent of fractionation is dependent on the concentration of the protein in the sample and the complexity of that sample.

LC-MS/MS based quantitation, including further separation on reversed phase (C18) nanoLC (PepMap C18; Dionex) and MS/MS: tandem mass spectrometry using MRM (4000 QTRAP; ABI)/SRM (Vantage TSQ; Thermo Scientific) mode. The LC column is connected to an electrospray needle connected to the source head of the mass spectrometer. As material elutes from the column, molecules are ionized and enter the mass spectrometer in the gas phase. The peptide that is monitored is specifically selected to pass the first quadrupole (Q1), based on its mass to charge ratio (m/z). The selected peptide is then fragmented in a second quadrupole (Q2) which is used as a collision cell. The resulting fragments then enter the third quadrupole (Q3). Depending on the instrument settings (determined during the assay development phase) only a specific peptide fragment or specific peptide fragments (or so called transitions) are selected for detection.

The combination of the m/z of the monitored peptide and the m/z of the monitored fragment of this peptide is called a transition. This process can be performed for multiple transitions during one experiment. Both the endogenous peptide (analyte) and its corresponding isotopically labelled synthetic peptide (internal standard) elute at the same retention time, and are measured in the same LC-MS/MS experiment.

The MASSterclass readout is defined by the ratio between the area under the peak specific for the analyte and the area under the peak specific for the synthetic isotopically labelled analogue (internal standard). MASSterclass readouts are directly related to the original concentration of the protein in the sample. MASSterclass readouts can therefore be compared between different samples and groups of samples.

A typical MASSterclass protocol followed in the present study is given here below:

25 µL of plasma is subjected to a depletion of human albumin and IgG (ProteoPrep spin columns; Sigma Aldrich) according to the manufacturer's protocol, except that 20 mM $NH_4HCO_3$ was used as the binding/equilibration buffer.

The depleted sample (225 µL) is denatured for 15 min at 95° C. and immediately cooled on ice 500 fmol of the isotopically labelled peptide (custom made 'Heavy AQUA' peptide; Thermo Scientific) is spiked in the sample 20 µg trypsin is added to the sample and digestion is allowed for 16 h at 37° C.

The digested sample was first diluted 1/8 in solvent A (0.1% formic acid) and then 1/20 in the same solvent containing 250 amol/µL of all isotopically labelled peptides (custom made 'Heavy AQUA' peptide; Thermo Scientific) of interest.

20 µL of the final dilution was separated using reverse-phase NanoLC with on-line MS/MS in MRM/SRM mode:

Column: PepMap C18, 75 µm I.D.×25 cm L, 100 Å pore diameter, 5 µm particle size

Solvent A: 0.1% formic acid

Solvent B: 80% acetonitrile, 0.1% formic acid

Gradient: 30 min; 2%-55% Solvent B

MS/MS in MRM mode: method contains the transitions for the analyte as well as for the synthetic, labelled peptide.

The used transitions were experimentally determined and selected during protein assay development Each of the transitions of interest was measured for a period starting 3 minutes before and ending 3 minutes after the determined retention time of the peptide of interest, making sure that each peak had at least 15 datapoints.

The raw data was analysed and quantified using the LCQuan software (Thermo Scientific): the area under the analyte (=the MCAM peptide) peak and under the internal standard (the labelled, synthetic MCAM peptide) peak at the same C18 retention time was determined by automatic peak detection. These were checked manually.

The MASSterclass readout was defined by the ratio of the analyte peak area and the internal standard peak area MASSterclass Statistical Analysis The measured ratios are differential quantitations of peptides. In other words a ratio is the normalised concentration of a peptide. The concentration of a peptide is proportional to the ratio measured with mass spectrometry.

Example 2

Verification of MCAM Using MASSterclass

Clinical samples were collected prospectively across 3 different medical centres from patients presenting to emergency department (ED) with acute dyspnea (n=100) either related to acute heart failure or related to other causes (=dyspnea non AHF).

For all included patients a comprehensive case report file (CRF) was completed with details on medical background, admission diagnosis and medications. An overview of the baseline patient characteristics is given in Table 1.

TABLE 1

|  |  | AHF | Dyspnea nonAHF |
|---|---|---|---|
| Age (av) |  | 72 ± 12 | 62 ± 19 |
| Gender | Males % | 67 | 64 |
| Medical history | HF history % | 70 | 8.5 |
|  | COPD/Asthma % | 14.5 | 20 |
|  | Coronary artery disease % | 30 | 4 |

TABLE 1-continued

| | | AHF | Dyspnea nonAHF |
|---|---|---|---|
| Physical examination | Heart Rate (bpm) | 84 (68-107) | 92 (75-114) |
| | Systolic bp (mmHg) | 135 (107-161) | 130 (106-145) |
| | Diastolic bp (mmHg) | 74 (61-87) | 70 (61-80) |
| ECG | LVEF - median (interquartile range) | 35 (25-51) | 65 (59-65) |
| Admission labs | BNP (pg/ml) | 1006 (470-2027) | 119.4 (57-297) |
| | NT-proBNP (pg/ml) | 5591 (2453-1500) | 670 (289-1939) |
| | Creatinine (umol/l) | 123.2 (89.5-161.5) | 79 (65-107.5) |
| Admission diagnosis | AHF | 52% | |
| | pneumonia | 20% | |
| | COPD/Asthma | 6% | |
| | pulmonary embolism | 3.50% | |
| | acute bronchitis | 2% | |
| | other (atrial fibrillation, ARDS, intoxication, . . .) | 13% | |
| | unknown | 3.50% | |

Receiver-operating characteristics (ROC) analysis demonstrated MCAM to be highly sensitive and specific for diagnosing AHF in dyspneic patients presenting to the ED, as indicated by an overall median AUC of 0.91 with 95% CI 0.85-0.96 (cf. FIG. 4). This diagnostic performance is equivalent to BNP and NT-proBNP, the current gold standard biomarkers for diagnosing AHF in an acute dyspnea population. Table 2 lists the results.

TABLE 2

| | BNP | NT-proBNP | MCAM |
|---|---|---|---|
| Median AUC | 0.88 | 0.85 | 0.91 |
| 95% CI | 0.82-0.95 | 0.77-0.92 | 0.85-0.96 |

The AHF population under study is enriched for patients with systolic dysfunction as indicated by the low median LVEF, i.e. 35%. These patients are typically more resistant to fluid build-up and hence represent to the ED with dyspnea caused by volume overload.

Example 3

Verification of MCAM as a Marker of Disease Progression and Filling Status: Comparison of Levels at Admission Versus Discharge Patients diagnosed with acute heart failure were sampled both at admission to the ED as well as at discharge from the hospital, i.e. when patients were deemed to have recovered and to be stable. On average the discharge sample was taken 9-11 days after the admission sample. Levels of MCAM were measured using MASSterclass in both samples and levels were compared within the same patient. For the majority of patients there was a significant decrease of MCAM when admission and discharge levels were compared (FIG. 2). A very similar picture is obtained when BNP levels at admission versus discharge are compared. This data supports the idea that MCAM levels are a reflection of disease status and thus could be used to monitor and/or predict an acute event.

Furthermore the main treatment given to these AHF patients are diuretics and as a consequence the patients lose fluids. Hence a drop in MCAM levels is reflective of a change in filling status of the patients.

Example 4

MCAM Levels Associate with Weight Gain and Weight Loss in Acute Dyspnea Patients Clinical samples from acute dyspnea patients (BASEL V cohort as described in Potocki et al., Journal of Internal Medicine 2010 January; 267(1):119-29), either diagnosed with acute decompensated heart failure or dyspnea due to other causes were screened for MCAM using MASSterclass. All clinical data pertaining the samples was obtained via the clinical collaborator and added to the MASSterclass data analysis pipeline.

Associations of MCAM levels with all available clinical parameters were computed using univariate statistical tests. Spearman's ranked test was used to compute correlation coefficients and Wilcoxon rank sum test for assessing whether two independent samples of observation originate from the same population.

This analysis showed a clear association of MCAM with weight gain prior to admission to the hospital and weight loss after therapeutic diuretics use as indicated by the low Wilcoxon p-values (summarized in Table 3).

TABLE 3

| | population | MCAM p-values |
|---|---|---|
| weight loss admission to discharge | AHF | 0.00383 |
| weight gain prior to admission | AHF | 0.00058 |

FIG. 6 illustrates the effect of weight gain on MCAM levels. AHF patients that put on weight prior to admission to the hospital (fluid build-up) have clearly increased levels of MCAM.

Example 5

MCAM Levels are Increased in AHF Patients with Systolic Dysfunction

Figure 7:
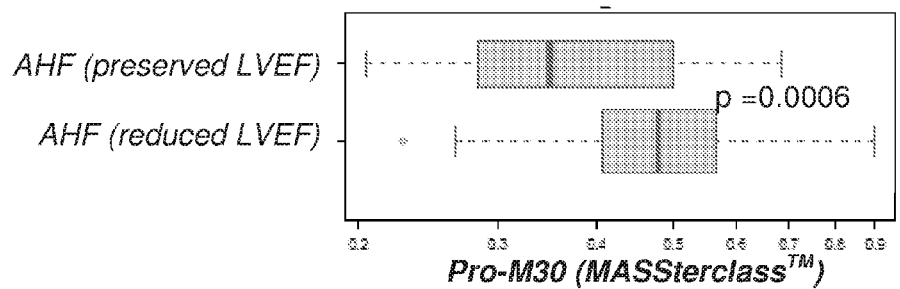
FIG. 7: illustrates in box and whisker plots the correlation between LVEF and MCAM levels in AHF patients at admission.

The effect of systolic versus diastolic dysfunction in heart failure patients on MCAM levels was investigated based on the MASSterclass screening results of the BASEL V cohort. This cohort contains a sufficient number of AHF patients with either reduced left ventricular ejection fraction (LVEF <55) or preserved LVEF (LVEF >55). MCAM levels are significantly higher in AHF patients with reduced ejection fractions (p<0.001). FIG. 7 shows box and whisker plots for MCAM in these two AHF subpopulations.

Patients with a systolic dysfunction (reduced EF) are more resistant to fluid build-up and will accumulate more volume compared to patients with diastolic dysfunction before symptoms of dyspnea occur.

Example 6

Correlation of MCAM Levels with LVEDP Value in Further Heart Failure Patient Cohorts A further patient cohort comprising a total of 223 patients with varying types and grades of cardiovascular disorders is studied, from which patients will be selected with different values of Left Ventricle End Diastolic Pressure (LVEDP). A correlation of LDEVP level with MCAM blood levels will be determined in said patients.

What is claimed is:

1. A method for treating impaired fluid homeostasis in a subject having symptoms of, being diagnosed with, or being at risk of developing heart failure, wherein the method comprises:
   a) identifying the subject as in need of treatment for impaired fluid homeostasis by a method comprising:
      (i) providing a sample from the subject;
      (ii) measuring the quantity of circulating melanoma cell adhesion molecule (MCAM) in the sample from the subject;
      (iii) comparing the quantity of circulating MCAM measured in (ii) with a reference value of the quantity of circulating MCAM, said reference value representing normal fluid homeostasis, and finding a deviation of the quantity of circulating MCAM measured in (ii) from said reference value so as to identify the subject as in need of the treatment, wherein an increased quantity of circulating MCAM in the sample from the subject compared to a reference value representing normal fluid homeostasis identifies the subject as in need of treatment of impaired fluid homeostasis; and
   b) treating the subject having the deviation, with a treatment or therapy that restores fluid homeostasis by decreasing the fluid content, selected from the group consisting of treatment with exogenous and/or endogenous diuretic agents, ultrafiltration, and treatment with exogenous and/or endogenous vasopressive antagonists.

2. The method according to claim 1, wherein said impaired fluid homeostasis is characterized by an increased or decreased vascular filling volume or pressure in said subject and/or a weight gain or weight loss due to fluid build-up or fluid drainage, respectively in said subject.

3. The method according to claim 1, wherein said impaired fluid homeostasis is caused by systolic dysfunction.

4. The method according to claim 3, wherein said systolic dysfunction is characterized by a decreased left ventricular ejection fraction (LVEF) and/or by increased cardiac filling pressure.

5. The method according to claim 1, wherein the identification step a) of the method further comprises measuring the quantity of one or more other biomarkers selected from the group consisting of B-type natriuretic peptide (BNP) and fragments or precursors thereof in the sample from the subject.

6. The method according to claim 1, wherein the quantity of circulating MCAM is measured using a binding agent capable of specifically binding to MCAM.

7. The method according to claim 1, wherein the quantity of MCAM is measured using an immunoassay technology, or using a mass spectrometry analysis method or using a chromatography method, or using a combination of said methods.

8. The method according to claim 1, wherein said sample is plasma, and wherein the plasma circulating form of MCAM is detected.

9. The method according to claim 1, wherein the heart failure is acute heart failure (AHF) or chronic heart failure (CHF).

10. The method according to claim 1, wherein the quantity of MCAM is measured using an antibody or aptamer specifically binding to circulating MCAM.

11. The method according to claim 1, wherein an increased quantity of MCAM in the sample from the subject compared to a reference value representing normal fluid homeostasis indicates that the subject is over-filled or is at risk of becoming over-filled, and wherein said therapy to restore fluid homeostasis by decreasing the fluid content, the vascular filling volume or pressure and/or reversing weight gain due to fluid build-up comprises administrating exogenous and/or endogenous diuretic agents, exogenous and/or endogenous vasopressive antagonists, and/or ultrafiltration to remove salts and the corresponding fluid from the circulation.

12. A method for treating impaired fluid homeostasis in a subject having symptoms of, being diagnosed with, or being at risk of developing heart failure, said subject being under treatment or having been under treatment, wherein the method comprises:
   a) Identifying the subject as being in need of further treatment of impaired fluid homeostasis by a method comprising:
      (i) providing blood samples taken from the subject at two or more successive time points;
      (ii) measuring the quantity of circulating melanoma cell adhesion molecule (MCAM) in said blood samples;
      (iii) comparing the quantity of circulating MCAM measured samples as measured in (ii) and finding a deviation or no deviation of the quantity of the circulating MCAM between said samples measured in (ii) so as to identify the subject as in need of the treatment;
      (iv) attributing said finding of deviation or no deviation in (iii) to a change in fluid homeostasis in the subject between the two or more successive time points
   b) treating the subject having the deviation, with a treatment or therapy that restores fluid homeostasis by decreasing the fluid content, selected from the group consisting of treatment with exogenous and/or endogenous diuretic agents, ultrafiltration, and treatment with exogenous and/or endogenous vasopressive antagonists,
      wherein an increase in quantity of circulating MCAM in the samples taken from said subject at successive time points identifies the subject as being in need of further treatment for fluid homeostasis, and
      wherein a decrease or normalisation in quantity of circulating MCAM in the samples taken from said subject at successive time points identifies the subject as no longer being in need of further treatment for fluid homeostasis.

13. The method according to claim 1, wherein the symptoms of heart failure are caused by volume overload.

* * * * *